US006852878B2

(12) United States Patent
Meng et al.

(10) Patent No.: US 6,852,878 B2
(45) Date of Patent: Feb. 8, 2005

(54) THIOKETALS AND THIOETHERS FOR INHIBITING THE EXPRESSION OF VCAM-1

(75) Inventors: Charles Q. Meng, Alpharetta, GA (US); Lee K. Hoong, Suwanee, GA (US); Patricia K. Somers, Fort Collins, CO (US)

(73) Assignee: Atherogenics, Inc., Alpharetta, GA (US)

(*) Notice: Subject to any disclaimer, the term of this patent is extended or adjusted under 35 U.S.C. 154(b) by 165 days.

(21) Appl. No.: 09/815,262

(22) Filed: Mar. 21, 2001

(65) Prior Publication Data

US 2002/0016300 A1 Feb. 7, 2002

Related U.S. Application Data

(63) Continuation-in-part of application No. 09/370,046, filed on Aug. 6, 1999, now Pat. No. 6,548,699, which is a continuation of application No. 09/079,213, filed on May 14, 1998, now Pat. No. 6,147,250.
(60) Provisional application No. 60/191,046, filed on Mar. 21, 2000.

(51) Int. Cl.$^7$ ............................................. C07C 309/00
(52) U.S. Cl. ............................. 562/42; 562/23; 562/11; 514/576
(58) Field of Search ............................. 568/38, 39, 45, 568/46, 47, 50

(56) References Cited

U.S. PATENT DOCUMENTS

| | | | |
|---|---|---|---|
| 3,179,701 A | | 4/1965 | Rocklin |
| 3,485,843 A | * | 12/1969 | Wang ........................ 544/403 |
| 3,576,883 A | * | 4/1971 | Neuworth .................... 568/47 |
| 3,704,327 A | * | 11/1972 | Neuworth .................... 568/47 |
| 3,897,500 A | * | 7/1975 | Neuworth .................... 568/47 |
| 4,076,841 A | | 2/1978 | Wagner et al. |
| 4,115,590 A | | 9/1978 | Lerner |
| 4,734,527 A | * | 3/1988 | Krauss ........................ 568/47 |
| 4,752,616 A | | 6/1988 | Hall et al. |
| 4,755,524 A | | 7/1988 | Mueller et al. |
| 4,954,514 A | | 9/1990 | Kita et al. |
| 5,206,247 A | | 4/1993 | Regnier et al. |
| 5,262,439 A | | 11/1993 | Parthasarathy |
| 5,294,724 A | | 3/1994 | Jendralla et al. |
| 5,627,205 A | | 5/1997 | Regnier et al. |
| 5,770,355 A | | 6/1998 | Brocia |
| 6,121,319 A | * | 9/2000 | Somers ........................ 514/548 |
| 6,147,250 A | | 11/2000 | Somers |
| 6,323,359 B1 | | 11/2001 | Jass |
| 6,448,019 B1 | | 9/2002 | Mendelsohn et al. |
| 6,548,699 B1 | * | 4/2003 | Somers ........................ 562/431 |

FOREIGN PATENT DOCUMENTS

| | | |
|---|---|---|
| DE | 27 16 125 A1 | 10/1977 |
| EP | 190 682 A2 | 8/1986 |
| EP | 212 310 A2 | 3/1987 |
| EP | 254 272 A2 | 1/1988 |
| EP | 292 660 A2 | 11/1988 |
| EP | 317 165 A1 | 5/1989 |
| EP | 348 203 A1 | 12/1989 |
| EP | 405 788 A2 | 1/1991 |
| EP | 418 648 A1 | 3/1991 |
| EP | 621 255 A1 | 10/1994 |
| EP | 763 527 A1 | 3/1997 |
| FR | 2.130.975 | 11/1972 |
| FR | 2.133.024 | 11/1972 |
| FR | 2.134.810 | 12/1972 |
| FR | 2.140.769 | 1/1973 |
| FR | 2.168.137 | 8/1973 |
| GB | 1136539 | 12/1968 |
| GB | 1148550 | 4/1969 |
| GB | 1199871 | 7/1970 |
| WO | WO 95/30415 A1 | 11/1995 |
| WO | WO 96/12703 A1 | 5/1996 |
| WO | WO 97/15546 A1 | 5/1997 |
| WO | WO 97/26258 A1 | 7/1997 |
| WO | WO 98/22418 A1 | 5/1998 |
| WO | WO 98/30255 A2 | 7/1998 |
| WO | WO 98/51289 A2 | 11/1998 |
| WO | WO 98/51662 A2 | 11/1998 |
| WO | WO 99/24400 A1 | 5/1999 |
| WO | WO 00/26184 A1 | 5/2000 |
| WO | WO 00/28332 A1 | 5/2000 |

OTHER PUBLICATIONS

U.S. Appl. No. 09/370,046, filed Aug. 6, 1999, Somers.

U.S. Appl. No. 09/436,892, filed Nov. 9, 1999, Medford et al., (Corrected Amendment and Response to Office Action dated Aug. 17, 2001.

U.S. Appl. No. 09/570,098, filed May 12, 2000, Patricia K. Somers, (Amendment and Response to Office Action dated May 12, 2000).

U.S. Appl. No. 09/779,086, filed Feb. 7, 2001, Chinery et al., (Substitute Specification and Drawings filed Jun. 18, 2001).

U.S. Appl. No. 09/833,407, filed Apr. 11, 2001, Luchoomun et al.

U.S. Appl. No. 10/060,734, filed Jan. 30, 2002, Patricia K. Somers, (Preliminary Amendment Filed Jan. 30, 2002).

U.S. Appl. No. 10/036,307, filed Oct. 25, 2001, Patricia K. Somers et al.

(List continued on next page.)

*Primary Examiner*—Samuel Barts
(74) *Attorney, Agent, or Firm*—Sherry M. Knowles, Esq.; King & Spalding, LLP

(57) ABSTRACT

Thioketals and thioethers are provided that inhibit the expression of VCAM-1, and which can be used in the treatment of VCAM-1 mediated diseases including inflammatory disorders, cardiovascular diseases, occular diseases, autoimmune diseases, neurological disorders, and cancer. The compounds also can be used to treat hyperlipidemia and/or hypercholesterolemia.

27 Claims, No Drawings

OTHER PUBLICATIONS

U.S. Appl. No. 10/114,346, filed Apr. 2, 2002, Charles Q. Meng, (Preliminary Amendment Filed Apr. 2, 2002).
U.S. Appl. No. 10/114,351, filed Apr. 2, 2002, Charles Q. Meng, (Preliminary Amendment Filed Apr. 2, 2002).
U.S. Appl. No. 10/115,206, filed Apr. 2, 2002, Charles Q. Meng, (Preliminary Amendment Filed Apr. 2, 2002).
U.S. Appl. No. 10/122,516, filed Apr. 11, 2002, Luchoomun et al.
Chemical Abstract, Database Chemabs Online!, Chemical Abstracts Service, Columbus, Ohio, US, STN, Accession No. 127:75973, XP002115597, see abstract; RN 1706–68–9 & V.Z. Lankin et al.: Dokl. Akad. Nauk, V. 351, No. 4, 1996, pp. 554–557.
Chemical Abstract, Database Chemabs Online!, Chemical Abstracts Service, Columbus, Ohio, US, STN, Accession No. 82:86196, XP002115598, see abstract; RN 54622–23–0, 54622–24–1 & Chemical Abstracts, vol. 82, No. 13, Mar. 31, 1975 (Mar. 1, 1975) Columbus, Ohio, US; Abstract No. 86196, XP002115592 abstract & JP 49 075552 A 9 (Sagami Chemical Research Center) Jul. 20, 1974.
Chemical Abstract, Database Chemabs Online!, Chemical Abstracts Service, Columbus, Ohio, US, STN, Accession No. 124:8690, XP00215603, see abstract; RN 171078–69–6, 171078–70–9, 171078–72–1,171078–73–2, 171078–75–4, 171078–76–5, 171078–77–6, 171078–78–7 & Chemical Abstracts, vol. 124, No. 1, Jan. 1, 1996, Columbus, Ohio, US; Abstract No. 8690, XP002115596 abstract & V.I. Kelarev et al.: Khim. Geterotsikl. Soedin, No. 4, 1995, pp. 514–517.
Chemical Abstract, Database Chemabs Online!, Chemical Abstracts Service, Columbus, Ohio, US, STN, Accession No. 124:146082, XP002115604, see abstract; RN 162933–21–3, 162933–22–4, 162933–23–5, 169180–32–9, 169180–34–1, 169180–36–3,173461–90–0, 173461–82—0, 173461–84–2, 173461–90–0, 173461–93–3, 173461–95–5 & V.I. Kelarev et al.: Khim. Geterotsikl. Soedin, No. 5, 1995, pp. 667–673.
Chemical Abstract, Database Chemabs Online!, Chemical Abstracts Service, Columbus, Ohio, US, STN, Accession No. 110:212254, XP002115683, see abstract; RN 100204–33–9, 111155–56–7, 9434–96–1, 120455–07–4, 120455–08–5, 120455–09–6, 120455–10–9 & Chemical Abstracts, vol. 110, No. 23, Jun. 5, 1989 Columbus, Ohio, US; Abstract No. 212254a, XP002115682 abstract & S.D. Pastor et al.: Phosphorous Sulfur, vol. 37, No. 3–4, 1988, pp. 117–123, L. Cominacini et al.: Free Radical Biology and Medicine, vol. 22, No. 1 –2, 1996, pp. 117–127, XP002095164, see figures 6–7.
Chemical Abstract, Database Chemabs Online!, Chemical Abstracts Service, Columbus, Ohio, US, STN, Accession No. 126:277465, XP002115599, see abstract; 188611–72–5, 188611–74–7, 188611–75–8, 188611–81–6, 188611–82–7 & Chemical Abstracts, vol. 126, No. 21, May 26, 1997 Columbus, Ohio, US; Abstract No. 277465, XP002115593 abstract & JP 09 059258 A (Ono Pharmaceutical Co) (Mar. 4, 1997).
Chemical Abstract, Database Chemabs Online!, Chemical Abstracts Service, Columbus, Ohio, US, STN, Accession No. 94:30290, XP00211560, see abstract; RN 76163–51–4 & CH. I. Mamedov: Mater. Nauchn. Konf. Aspir. Akad. Nauk Az. SSR, vol. 1, 1980, pp. 127–131.

Chemical Abstract, Database Chemabs Online!, Chemical Abstracts Service, Columbus, Ohio, US, STN, Accession No. 86:5066, XP002115601, see abstract; RN 55109–77–8, 61151–55–1 & Chemical Abstracts, vol. 86, No. 1, Jan. 3, 1977 Columbus, Ohio, US; Abstract No. 5066, XP002115594, abstract & A.I. Medvedev et al.: Tezisy Dokl. Nauchn. Sess. Khim. Teknol. Org. Soedin. Sery Sernistykh Neftei, 13$^{th}$, 1974, pp. 123–124.

Chemical Abstract, Database Chemabs Online!, Chemical Abstracts Service, Columbus, Ohio, US, STN, Accession No. 122:187387, XP002115602, see abstract; RN 161523–77–9, & Chemical Abstracts, vol. 122, No. 15, Apr. 10, 1995 Columbus, Ohio, US; Abstract No. 187387, XP002115595 abstract & JP 06 312978 A (Nippon Tobacco Sangyo et al) Nov. 8, 1994.

Chemical Abstrct, Database Chemabs Online!, Chemical Abstracts Service, Columbus, Ohio, US, STN, CAPLUS Accession No. 1970:445047, XP002124423, see abstract; RN 27428–10–0, 27428–13–3, 27428–14–4, 27428–15–5, 27428–16–6, 27428–17–7, 27428–18–8, 27428–19–9 & M. B. Neuworth et al.: J. Med. Chem., V. 13, No. 4, 1970, pp. 722–725.

Chemical Abstract, Database Chemabs Online!, Chemical Abstracts Service, Columbus, Ohio, US, STN, CAPLUS Accession No. 1986:28675, XP002124424, see abstract; RN 99661–86–6, 99661–87–7, 27466–44–0 & Chemical Abstracts, vol. 104, No. 5, Feb. 3, 1986, Columbus, Ohio, US; Abstract No. 28675, abstract & P. De Meglio et al.: Farmaco, Ed. Sci., vol. 40, No. 11, 1985, pp. 833–844.

Cominacini et al., "Antioxidants Inhibit the Expression of Intercellular Cell Adhesion molecule–1 and Vascular Cell Adhesion Molecule–1 Induced by Oxidized LDL on Human Umbilical Vein Endothelial Cells," *Free Radical Biology & Medicine*, vol. 22, Nos. 1/2, pp. 117–127, 1997.

Feldman, Davis, et al., "The In Vitro and Ex Vivo Antioxidant Properties, and Hypolipidemic Activity of CGP 2881," *Atherosclerosis*, Dec. 28, 1998, vol. 144, pp. 343–355.

Fruebis, Joachim, "A Comparison of the Antiatherogenic Effects of Probucol and of a Structural Analogue of Probucol in Low Density Lipoprotein Receptor–deficient Rabbits," *The American Society for Clinical Investigation, Inc.*, Jul. 1994, vol. 94, pp. 392–398.

Mao et al., "Antioxidant Activity of Probucol and Its Analogues in Hypercholesterolemic Watanabe Rabbits," *Journal of Medicinal Chemistry*, Jan. 1991, vol. 34, No. 1, pp. 298–302.

Mao et al. "Attenuation of Atherosclerosis in a Modified Strain of Hypercholesterolemic Watanabe Rabbits with Use of a Probucol Analogue (MDL29,311) That Does Not Lower Serum Cholesterol," *Arteriosclerosis and Thrombosis*, Sep./Oct. 1991, vol. 11, No. 5, pp. 1266–1275.

Ramasamy, Santhini et al., "Modulation of Expression of Endothelial Nitric Oxide Synthase by Nordihydroguaiaretic Acid, a Phenolic Antioxidant in Cultured Endothelial Cells," *Molecular Pharmacology*, Apr. 5, 1999, vol. 56, pp. 116–123.

* cited by examiner

THIOKETALS AND THIOETHERS FOR INHIBITING THE EXPRESSION OF VCAM-1

RELATIONSHIP TO PRIOR APPLICATIONS

This application claims priority to U.S. Provisional Patent Application No. 60/191,046, filed on Mar. 21, 2000. This application is also a continuation-in-part of U.S. application Ser. No. 09/370,046, filed Aug. 6, 1999, now U.S. Pat. No. 6,548,699, which is a continuation of U.S. application Ser. No. 09/079,213, filed May 14, 1998, now U.S. Pat. No. 6,147,250.

FIELD OF THE INVENTION

This invention is in the area of compounds, compositions and methods for inhibiting the expression of VCAM-1 and, in particular, for treating diseases mediated by VCAM-1, including inflammatory disorders, cardiovascular diseases, occular diseases, autoimmune diseases, neurological disorders, and cancer. The invention is further in the area of compounds, compositions and for treating hypercholesterolemia and hyperlipidemia.

BACKGROUND OF THE INVENTION

Expression of VCAM-1

Adhesion of leukocytes to the endothelium represents a fundamental, early event in a wide variety of inflammatory conditions, including atherosclerosis, autoimmune disorders and bacterial and viral infections. Leukocyte recruitment to the endothelium is started when inducible adhesion molecule receptors on the surface of endothelial cells interact with counterreceptors on immune cells. Vascular endothelial cells determine which type of leukocytes (monocytes, lymphocytes, or neutrophils) are recruited, by selectively expressing specific adhesion molecules, such as vascular cell adhesion molecule-1 (VCAM-1), intercellular adhesion molecule-1 (ICAM-1), and E-selectin. In the earliest stage of the atherosclerotic lesion, there is a localized endothelial expression of VCAM-1 and selective recruitment of mononuclear leukocytes that express the integrin counterreceptor VLA-4. Because of the selective expression of VLA-4 on monocytes and lymphocytes, but not neutrophils, VCAM-1 is important in mediating the selective adhesion of mononuclear leukocytes. Subsequent conversion of leukocytes to foamy macrophages results in the synthesis of a wide variety of inflammatory cytokines, growth factors, and chemoattractants that help propagate the leukocyte and platelet recruitment, smooth muscle cell proliferation, endothelial cell activation, and extracellular matrix synthesis characteristic of maturing atherosclerotic plaque.

VCAM-1 is also a mediator of chronic inflammatory disorders such as asthma, rheumatoid arthritis, autoimmune diabetes and multiple sclerosis. For example, it is known that the expression of VCAM-1 and ICAM-1 are increased in asthmatics (Pilewski, J. M., et al. *Am. J. Respir. Cell Mol. Biol.* 12, 1–3 (1995); Ohkawara, Y., et al., *Am. J. Respir. Cell Mol. Biol.* 12, 4–12 (1995)). Additionally, blocking the integrin receptors for VCAM-1 and ICAM-1 (VLA-4 and LFA-1, respectively) suppressed both early and late phase responses in an ovalbumin-sensitized rat model of allergic airway responses (Rabb, H. A., et al., *Am. J. Respir. Care Med.* 149, 1186–1191 (1994)). There is also increased expression of endothelial adhesion molecules, including VCAM-1, in the microvasculature of rheumatoid synovium (Koch, A. E. et al., *Lab. Invest.* 64, 313–322 (1991); Morales-Ducret, J. et al., *Immunol.* 149, 1421–1431 (1992)). Neutralizing antibodies directed against VCAM-1 or its counter receptor, VLA-4, can delay the onset of diabetes in a mouse model (NOD mice) which spontaneously develop the disease (Yang, X. D. et al., *Proc. Natl. Acad. Sci. U.S.A.* 90, 10494–10498 (1993); Burkly, L. C. et al., *Diabetes* 43, 523–534 (1994); Baron, J. L. et al., *J. Clin. Invest.* 93, 1700–1708 (1994)).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea (Koch, A. F. et al., *Nature* 376, 517–519 (1995)). Inhibitors of the expression of soluble VCAM-1 have potential therapeutic value in treating diseases with a strong angiogenic component, including tumor growth and metastasis (Folkman, J., and Shing, Y., *Biol Chem.* 10931–10934 (1992)).

VCAM-1 is expressed in cultured human vascular endothelial cells after activation by lipopolysaccharide (LPS) and cytokines such as interleukin-1 (IL-1) and tumor necrosis factor (TNF-alpha). These factors are not selective for activation of cell adhesion molecule expression.

It has been documented that VCAM-1 is expressed on brain microvessel endothelial cells in active lesions of multiple sclerosis brain. Multiple sclerosis is a common demyelinating disorder for the central nervous system, causing patches of sclerosis (plaques) in the brain and spinal cord. It occurs in young adults and has protean clinical manifestations. Experimental therapy using antibodies for VCAM-1 in autoimmune encephalomyelitis, which is an animal model for multiple sclerosis, has shown that adhesion molecules play a role in the pathogenesis of the disease (Benveniste et al., *J. Neuroimmunol.* 98:77–88, 1999). Time and dose dependent expression of VCAM-1 and release of soluble VCAM-1 were detected in cultures of human cerebral endothelial cells induced by TNF-alpha, but not in peripheral blood mononuclear cells (Kallmann et al., *Brain* 123:687–697, 2000). Clinical data also show that adhesion molecules in blood and cerebrospinal fluid are up-regulated throughout the clinical spectrum of multiple sclerosis, further supporting the belief that multiple sclerosis can be suppressed by interfering with cell adhesion molecules such as VCAM-1 (Elovaara et al., *Arch. Neurol.* 57:546–551, 2000).

Cell adhesion molecules have also been shown to play an important role in recruiting T lymphocytes to graft endothelium on transplanted vascularized tissue and organs, and have thus been implicated in organ transplant rejections and allograft rejections. Expression on VCAM-1 and ICAM-1 in normal cardiac tissue is very limited in vascular endothelium. However, immunohistochemical studies on transplanted allografts have revealed that increased expression of these molecules on the vascular endothelium and on cardiac myocytes occurs from the early stages of graft rejection in human and animal transplants (Cosimi et al., *J. Immunol.* 144: 4604–4612, 1990; Orosz et al., *Transplantation* 56:453–460, 1993; Pelletier et al., *Transplant Proc.* 25: 839–841, 1993; Tanio et al. *Circulation* 89:1760–1768, 1994). In a murine heart transplant model, the survival rate of mice treated with anti-VCAM-1 monoclonal antibodies or anti-VLA-4 monoclonal antibodies was greater than the survival rate of a control group (Isobe et al., *J. Immunol.* 153: 5810–5818, 1994; Orosz et al., *J. Heart Lung Transplant* 16: 889–904, 1997).

Hypercholesterolemia and Hyperlipidemia

Hypercholesterolemia is an important risk factor associated with cardiovascular disease. Serum lipoproteins are the carriers for lipids in the circulation. Lipoproteins are classified according to their density: chylomicrons, very low-density lipoproteins (VLDL), low density lipoproteins (LDL) and high-density lipoproteins (HDL). Chylomicrons primarily participate in transporting dietary triglycerides and cholesterol from the intestine to adipose tissue and liver. VLDL deliver endogenously synthesized triglycerides from liver to adipose and other tissues. LDL transports cholesterol to peripheral tissues and regulates endogenous cholesterol levels in those tissues. HDL transports cholesterol from peripheral tissues to the liver. Arterial wall cholesterol is derived almost exclusively from LDL. Brown and Goldstein, *Ann. Rev. Biochem.* 52, 223 (1983); Miller, *Ann. Rev. Med.* 31, 97 (1980).

Steinberg, et al., (N. Eng. J. Med. 1989; 320:915–924) hypothesized that modification of low-density lipoprotein (LDL) into oxidatively modified LDL (ox-LDL) by reactive oxygen species is the central event that initiates and propagates atherosclerosis. Oxidized LDL is a complex structure consisting of at least several chemically distinct oxidized materials, each of which, alone or in combination, may modulate cytokine-activated adhesion molecule gene expression. Fatty acid hydroperoxides such as linoleyl hydroperoxide (13-HPODE) are produced from free fatty acids by lipoxygenases and are an important component of oxidized LDL.

Through a mechanism that is not well defined, areas of vessel wall predisposed to atherosclerosis preferentially sequester circulating LDL. Through a poorly understood pathway, endothelial, smooth muscle, and/or inflammatory cells then convert LDL to ox-LDL. In contrast to LDL, which is taken up through the LDL receptor, monocytes avidly take up ox-LDL through a "scavenger" receptor whose expression, unlike the LDL receptor, is not inhibited as the content of intracellular lipid rises. Thus, monocytes continue to take up ox-LDL and become lipid-engorged macrophage-foam cells that form the fatty streak.

Typically, cholesterol is carried in the blood of warm-blooded animals in certain lipid-protein complexes such as chylomicrons, very low density lipoprotein (VLDL), low density lipoprotein (LDL), and high density lipoprotein (HDL). It is widely accepted that LDL functions in a way that directly results in deposition of the LDL cholesterol in the blood-vessel wall and that HDL functions in way that results in the HDL picking up cholesterol from the vessel wall and transporting it to the liver where it is metabolized (Brown and Goldstein, *Ann. Rev. Biochem.* 52, 223 (1983); Miller, *Ann. Rev. Med.* 31, 97 (1980)). For example, in various epidemiologic studies the LDL cholesterol levels correlate well with the risk of coronary heart disease whereas the HDL cholesterol levels are inversely associated with coronary heart disease (Patton et al., *Clin. Chem.* 29, 1980 (1983)). In patients with low levels of LDL, the development of atherosclerosis is rare.

Furthermore, there is evidence based on animal and laboratory findings that peroxidation of LDL lipid, such as the unsaturated fatty acid portions of LDL cholesteryl esters and phospholipids, facilitate the accumulation of cholesterol in monocyte/macrophages which eventually are transformed into foam cells and become deposited in the sub-endothelial space of the vessel wall. The accumulation of foam cells in the vessel wall is recognized as an early event in the formation of an atherosclerotic plaque. Thus it is believed that peroxidation of LDL lipid is an important prerequisite to the facilitated accumulation of cholesterol in the vessel wall and the subsequent formation of an atherosclerotic plaque. (Parthasarathy et al., *J. Clin. Invest.* 77,641 (1986)). It is therefore desirable to provide methods of inhibiting LDL lipid peroxidation in a patient in need thereof.

Elevated cholesterol levels are associated with a number of disease states, including restenosis, angina, cerebral atherosclerosis, and xanthoma. It is desirable to provide a method for reducing plasma cholesterol in patients with, or at risk of developing, restenosis, angina, cerebral arteriosclerosis, xanthoma, and other disease states associated with elevated cholesterol levels.

There are several drug classes that are commonly used to lower LDL levels, including bile acid sequestrants, nicotinic acid (niacin), and 3-hydroxy-3-methylglutaryl coenzyme A (HMG CoA) reductase inhibitors (statins). Statins are among the most effective agents currently on the market for hypercholesterolemia, and include pravastatin (Pravchol, Bristol Myers Squibb), atorvastatin (Warner Lambert/Pfizer), simvastatin (Zocor, Merck), lovastatin (Mevacor, Merck), and fluvastatin (Lescol).

Probucol has been shown to possess potent antioxidant properties and to block oxidative modification of LDL. Consistent with these findings, probucol has been shown to actually slow the progression of atherosclerosis in LDL receptor-deficient rabbits as discussed in Carew et al. Proc. Natl. Acad. Sci. U.S.A. 84:7725–7729 (1987).

Probucol is chemically related to the widely used food additives 2, (3)-tert-butyl-4-hydroxyanisole (BHA) and 2,6-di-tert-butyl-4-methyl phenol (BHT). It is a thioketal having a chemical name of 4,4'-(isopropylidenedithio) bis(2,6-di-tert-butylphenol) and has the following chemical structure:

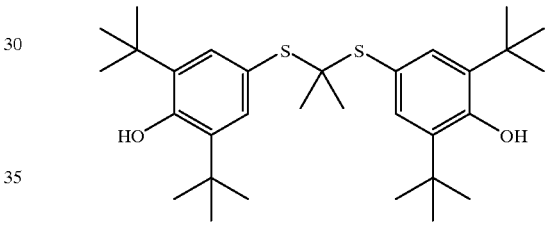

Probucol is used primarily to lower serum cholesterol levels in hypercholesterolemic patients. Probucol is commonly administered in the form of tablets available under the trademark Lorelco™.

U.S. Pat. No. 5,262,439 to Parthasarathy discloses analogs of probucol with increased water solubility in which one or both of the hydroxyl groups are replaced with ester groups.

A series of French patents disclose that certain probucol ester derivatives are hypocholesterolemic and hypolipemic agents: Fr 2168137 (bis 4-hydroxyphenylthioalkane esters); Fr 2140771 (tetralinyl phenoxy alkanoic esters of probucol); Fr 2140769 (benzofuryloxyalkanoic acid derivatives of probucol); Fr 2134810 (bis-(3-alkyl-5-t-alkyl-4-thiazole-5-carboxy)phenylthio)alkanes; FR 2133024 (bis-(4-nicotinoyloxyphenylthio)propanes; and Fr 2130975 (bis(4-(phenoxyalkanoyloxy)-phenylthio)alkanes).

De Meglio et al., have described several ethers of symmetrical molecules for the treatment of hyperlipidemia. These molecules contain two phenyl rings attached to each other through a —S—C(CH$_3$)$_2$—S— bridge. In contrast to probucol, the phenyl groups do not have t-butyl as substituents. (De Meglio et al., *New Derivatives of Clofibrate and probucol: Preliminary Studies of Hypolipemic Activity*; Farmaco, Ed. Sci (1985), 40 (11), 833–44).

WO 00/26184 disclosed a large genus of compounds with a general formula of phenyl-S-alkylene-S-phenyl, in which one or both phenyl rings can be substituted at any position. These compounds were disclosed as lubricants.

U.S. Pat. Nos. 5,750,351; 5,807,884; 5,811,449; 5,846,959; 5,773,231, and 5,773,209 to Medford, et al. (assigned to Emory University), as well as the corresponding WO95/30415 to Emory University indicate that polyunsaturated fatty acids ("PUFAs") and their hydroperoxides ("ox-PUFAs"), which are important components of oxidatively modified low density lipoprotein (LDL), induce the expression of VCAM-1, but not intercellular adhesion molecule-1 (ICAM-1) or E-selectin in human aortic endothelial cells, through a mechanism that is not mediated by cytokines or other noncytokine signals.

U.S. Pat. No. 5,155,250 to Parker, et al. discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 to Parker, et al. discloses that alkylated-4-silyl-phenols inhibit the peroxidation of LDL, lower plasma cholesterol, and inhibit the expression of VCAM-1, and thus are useful in the treatment of atherosclerosis.

A series of European patent applications of Shionogi Seiyaku Kabushiki Kaisha disclose phenolic thioethers for use in treating arteriosclerosis. European Patent Application No. 348 203 discloses phenolic thioethers which inhibit the denaturation of LDL and the incorporation of LDL by macrophages. The compounds are useful as anti-arteriosclerosis agents. Hydroxamic acid derivatives of these compounds are disclosed in European Patent Application No. 405 788 and are useful for the treatment of arteriosclerosis, ulcer, inflammation and allergy. Carbamoyl and cyano derivatives of the phenolic thioethers are disclosed in U.S. Pat. No. 4,954,514 to Kita, et al.

U.S. Pat. No. 4,752,616 to Hall, et al., discloses arylthioalkylphenylcarboxylic acids for the treatment of thrombotic disease. The compounds disclosed are useful as platelet aggregation inhibitors for the treatment of coronary or cerebral thromboses and the inhibition of bronchoconstriction, among others.

A series of patents to Adir et Compagnie disclose substituted phenoxyisobutyric acids and esters useful as antioxidants and hypolipaemic agents. This series includes U.S. Pat. Nos. 5,206,247 and 5,627,205 to Regnier, et al. (which corresponds to European Patent Application No. 621 255) and European Patent Application No. 763 527.

WO 97/15546 to Nippon Shinyaku Co. Ltd. discloses carboxylic acid derivatives for the treatment of arterial sclerosis, ischemic heart diseases, cerebral infarction and post PTCA restenosis.

The Dow Chemical Company is the assignee of patents to hypolipidemic 2-(3,5-di-tert-butyl-4-hydroxyphenyl)thio carboxamides. For example, U.S. Pat. Nos. 4,029,812, 4,076,841 and 4,078,084 to Wagner, et al., disclose these compounds for reducing blood serum lipids, especially cholesterol and triglyceride levels.

PCT WO 98/51289, filed by Emory University and listing as inventors Russell M. Medford and Patricia K. Somers, claims priority to provisional patent application U.S. Ser. No. 60/047,020, filed on May 14, 1997. This application discloses that monoesters of probucol inhibit the expression of VCAM-1, and may also exhibit the composite profile of lowering LDL and reducing cholesterol.

Given that cardiovascular disease is currently the leading cause of death in the United States, and ninety percent of cardiovascular disease is presently diagnosed as atherosclerosis, there is a strong need to identify new methods and pharmaceutical agents for its treatment. Moreover, given the growing body of evidence implicating inflammation and VCAM-1 expression in cardiovascular disease and other disease states such as rheumatoid arthritis, multiple sclerosis, and allograft rejection, there is also a need to identify methods and pharmaceutical agents for reducing inflammation and VCAM-1 expression.

It is therefore an object of the invention to provide methods of treating disorders and diseases mediated by VCAM-1, including cardiovascular and inflammatory diseases.

It is also an object to provide new classes of compounds and pharmaceutical compositions for the treatment of diseases and disorders mediated by the expression of VCAM-1.

It is a further object of the present invention to provide methods, compounds, and compositions for the treatment of hypercholesterolemia and/or hyperlipidemia.

It is also an object of the present invention to provide new classes of thioketal and thioether compounds, and pharmaceutical uses of such compounds.

SUMMARY OF THE INVENTION

Thioketals and thioethers of formulas (I) and (II) have been discovered that inhibit the expression of VCAM-1, and which can thus be used to treat patients with disorders mediated by VCAM-1. The invention provides:

(i) defined thioketals and thioethers, and pharmaceutical formulations comprising such thioketals and thioethers;

(ii) the use of thioketals and thioethers in the treatment of diseases mediated by VCAM-1;

(iii) the use of thioketals and thioethers in the treatment of inflammatory disorders (including but not limited to rheumatoid arthritis, osteoarthritis, inflammatory bowel disease, Crohn's disease, asthma, allergic rhinitis, sinusitis, chronic obstructive pulmonary disease (COPD), dermatitis, psoriasis, cystic fibrosis, multiple sclerosis, vasculitis, and organ transplant rejection);

(iv) the use of thioethers and thioketals in the treatment of cardiovascular diseases (including but not limited to atherosclerosis, post-angioplasty restenosis, coronary artery disease, angina, small artery disease, diabetes mellitus, diabetic nephropathy, and diabetic retinopathy);

(v) the use of thioethers and thioketals in the treatment of occular diseases (including but not limited to uveitis and macular degeneration);

(vi) the use of thioethers and thioketals in the treatment of automimmune diseases (including but not limited to systemic lupus erythematosus, type 1 diabetes, and graft versus host disease);

(vii) the use of thioethers and thioketals in the treatment of neurological diseases (including but not limited to Alzheimer's disease, Parkinson's disease, and amyotrophic lateral sclerosis (ALS);

(viii) the use of thioethers and thioketals in the treatment of cancer (including but not limited to tumor metastasis and angiogenesis); and (ix) the use of thioketals and thioethers in the treatment of hypercholesterolemia and/or hyperlipidemia.

In one embodiment the compounds of the present invention are thioketals represented by formula (I), and pharmaceutically acceptable salts thereof:

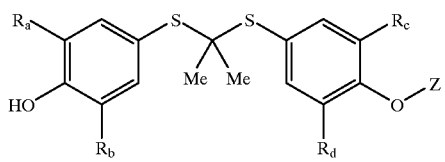

(I)

wherein a) $R_a$, $R_b$, $R_c$, and $R_d$ are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and b) Z is (i) a substituted or unsubstituted carbohydrate, (ii) a substituted or unsubstituted alditol, (iii) $C_{1-10}$alkyl or substituted $C_{1-10}$alkyl, terminated by sulfonic acid, (iv) $C_{1-10}$alkyl or substituted $C_{1-10}$alkyl, terminated by phosphonic acid, (v) substituted or unsubstituted $C_{1-10}$alkyl-O—C(O)—$C_{1-10}$alkyl, (vi) straight chained polyhydroxylated $C_{3-10}$alkyl; (vii) —$(CR_2)_{1-6}$—COOH, wherein R is independently hydrogen, halo, amino, or hydroxy, and wherein at least one of the R substituents is not hydrogen; or (viii) —$(CR_2)_{1-6}$—X, wherein X is aryl, heteroaryl, or heterocycle, and R is independently hydrogen, halo, amino, or hydroxy.

In another embodiment the compounds of the present invention are thioethers and related compounds represented by formula (II), and their pharmaceutically acceptable salts:

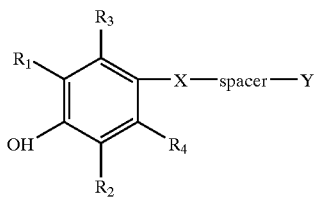

(II)

wherein:

a) X is O, S, SO, $SO_2$, $CH_2$, or NH;

b) spacer is —$(CH_2)_n$—, —$(CH_2)_n$—CO—$(CH_2)_n$—NH—, —$(CH_2)_n$—O—, —$(CH_2)_n$—S—, —$(CH_2O)$—, —$(OCH_2)$—, —$(SCH_2)$—, —$(CH_2S—)$, —(aryl-O)—, —(O-aryl)—, —(alkyl-O)—, —(O-alkyl)—; —O—C(O)—, —S—C(S)—, —C(O)—O—, —C(S)—S— c) n is 0, 1, 2, 3, 4, 5, 6, 7, 8, 9, or 10;

d) $R^1$ and $R^2$ are independently straight chained, branched, or cyclic alkyl which may be substituted, aryl, substituted aryl, heteroaryl, substituted heteroaryl, alkaryl, or aralkyl;

e) $R^3$ and $R^4$ are independently any group that does not otherwise adversely affect the desired properties of the molecule, including H, halogen, alkyl, substituted alkyl, aryl, substituted aryl, heteroaryl, substituted heteroaryl, alkaryl, or aralkyl; and f) Y is aryl or heteroaryl monosubstituted by —C(O)$NR_5R_6$, wherein $R_5$ and $R_6$ are independently hydrogen or alkyl.

DETAILED DESCRIPTION OF THE INVENTION

Active Compounds

In one embodiment of the invention, there are provided compounds of formula (I), and pharmaceutically acceptable salts thereof:

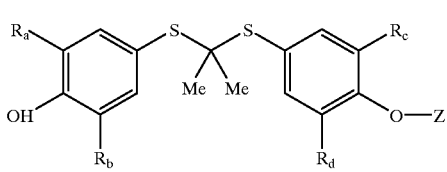

(I)

wherein a) $R_a$, $R_b$, $R_c$, and $R_d$ are independently any group that does not adversely affect the desired properties of the molecule, including hydrogen, alkyl, substituted alkyl, aryl, substituted aryl, heteroaryl, substituted heteroaryl, alkaryl, substituted alkaryl, aralkyl, or substituted aralkyl; and b) Z is (i) a substituted or unsubstituted carbohydrate, (ii) a substituted or unsubstituted alditol, (iii) $C_{1-10}$alkyl or substituted $C_{1-10}$alkyl, terminated by sulfonic acid, (iv) $C_{1-10}$alkyl or substituted $C_{1-10}$alkyl, terminated by phosphonic acid, (v) substituted or unsubstituted $C_{1-10}$alkyl—O—C(O)-$C_{1-10}$alkyl, (vi) straight chained polyhydroxylated $C_{3-10}$alkyl; (vii) —$(CR_2)_{1-6}$—COOH, wherein R is independently hydrogen, halo, amino, or hydroxy, and wherein at least one of the R substituents is not hydrogen; or (viii) —$(CR_2)_{1-6}$—X, wherein X is aryl, heteroaryl, or heterocycle, and R is independently hydrogen, halo, amino, or hydroxy.

$R_a$, $R_b$, $R_c$, and $R_d$ are in one embodiment selected independently from substituted and unsubstituted lower alkyl, in one embodiment branched lower alkyl. When $R_a$, $R_b$, $R_c$, and $R_d$ are substituted, they are in one embodiment substituted by halogen, alkyl, nitro, amino, haloalkyl, alkylamino, dialkylamino, acyl, or acyloxy. In one particular embodiment $R_a$, $R_b$, $R_c$, and $R_d$ are all t-butyl.

Z can be selected from any type of naturally occurring or synthetic carbohydrate as that term is conventionally used and understood. The term carbohydrate generally refers to a compound of carbon, hydrogen, and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment the carbohydrates are monosaccharides. In another embodiment the carbohydrates are pyranose and furanose sugars.

Non limiting examples of pyranose and furanose sugars within the scope of the present invention include threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine.

The carbohydrate can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate, phosphonic acid, phosphonate, or any other viable functional group that does not inhibit the pharmacological activity of this compound. Exemplary substituents include amine and halo, particularly fluorine. The substituent or carbohydrate can be either unprotected, or protected as necessary, as known to those skilled in the art, for example, as taught in Greene, et al., *Protective Groups in Organic Synthesis*, John Wiley and Sons, Second Edition, 1991, hereby incorporated by reference. In one embodiment the monosaccharide is a furanose such as (L or D)-ribose. In an even more particular embodiment Z is ribofuranose.

Z can also be selected from any type of naturally occurring or synthetic alditols as that term is conventionally used and understood. The term alditol generally refers to a carbohydrate in which the aldehyde or ketone group has been reduced to an alcohol moiety. The alditols of the present invention can also be optionally substituted or deoxygenated at one or more positions. The alditol may comprise 3, 4, 5, 6, or 7 carbons. Examples of useful alditols are those derived from reduction of monosaccharides. In another embodiment the carbohydrates are derived from reduction of pyranose and furanose sugars. One particular alditol is the arabitol analog of the formula where Z is —$CH_2$—$(CHOH)_3CH_2OH$. Another particular alditol is represented by the formula —$CH_2$—$(CHOH)_4CH_2OH$.

Exemplary structures for Z include the carbohydrates presented below in Table I and the alditols presented below in Table II.

TABLE I

Z
Cyclic Monosaccharides and Monosaccharide Derivatives

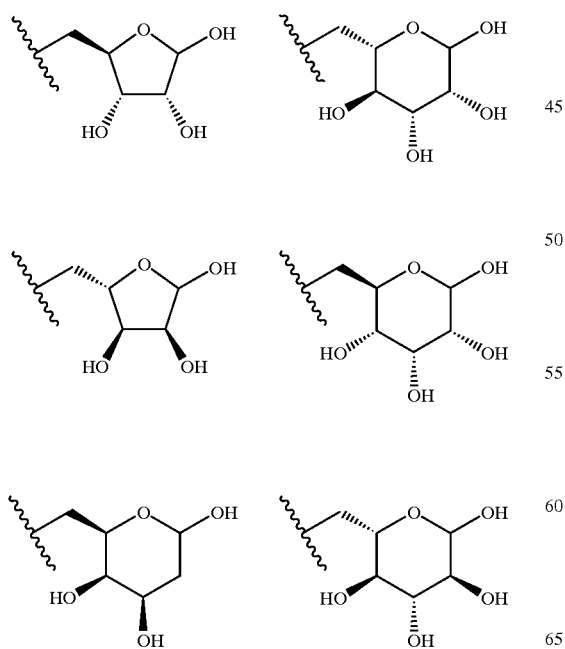

TABLE I-continued

Z
Cyclic Monosaccharides and Monosaccharide Derivatives

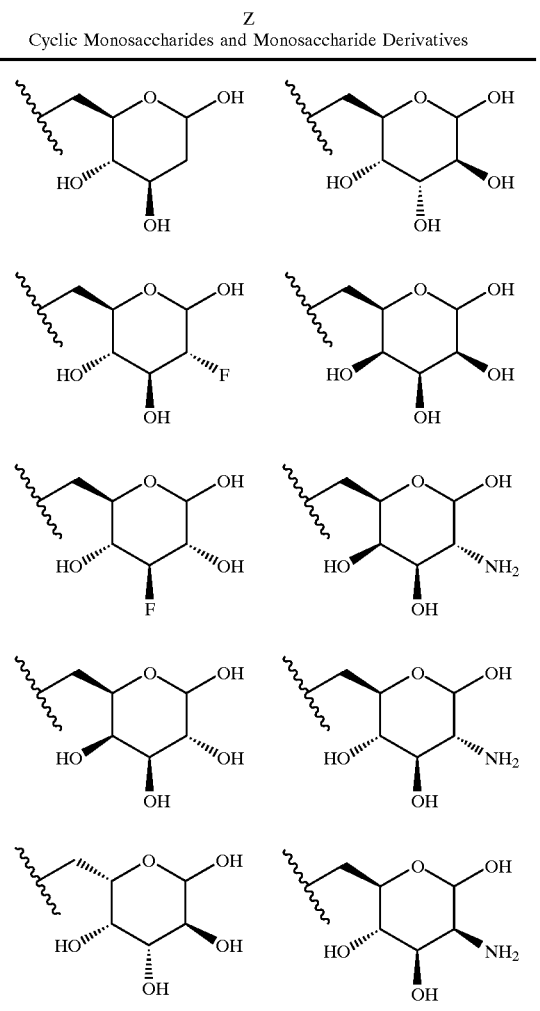

TABLE II

Z
Acyclic Monosaccharides Analogs

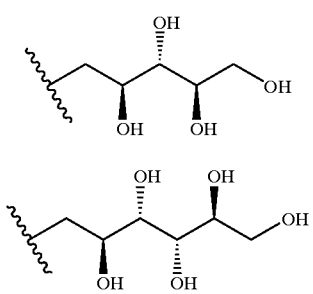

TABLE II-continued

Z
Acyclic Monosaccharides Analogs

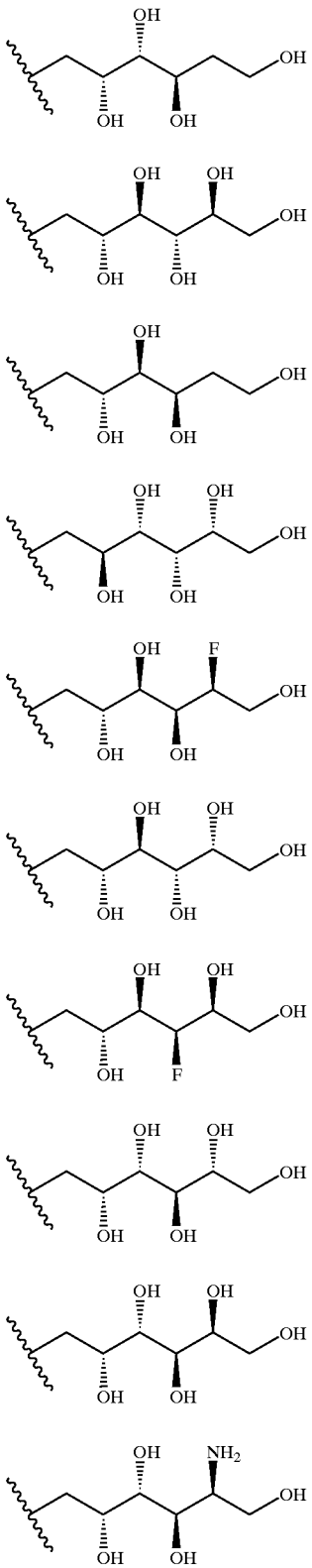

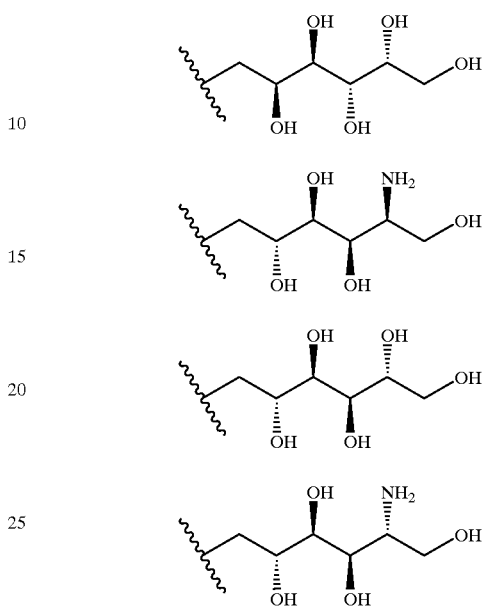

Z may also be alkyl or substituted alkyl that terminates in sulfonic acid. Z terminates in sulfonic acid when the longest chain of carbon atoms in an alkyl moiety, beginning at the oxygen in formula (I), terminates in sulfonic acid. When the alkyl moiety is substituted, it is suitably substituted by halogen, hydroxy, alkyl, nitro, amino, haloalkyl, alkylamino, dialkylamino, acyl, or carboxy. A particular sulfonic acid moiety Z is $(CR_2)_{1-6}$-sulfonic acid, wherein R is independently hydrogen, halo, amino, or hydroxy. In an even more particular embodiment Z is $(CR_2)_{1-4}$-sulfonic acid, wherein R is independently hydrogen or hydroxy. An even more particular sulfonic acid moiety Z is 2-hydroxypropyl-3-sulfonic acid.

Z may also be alkyl or substituted alkyl that terminates in phosphonic acid. Z terminates in phosphonic acid when the longest chain of carbon atoms in an alkyl moiety, beginning at the oxygen in formula (I), terminates in phosphonic acid. When the alkyl moiety is substituted, it is in one embodiment substituted by halogen, hydroxy, alkyl, nitro, amino, haloalkyl, alkylamino, dialkylamino, acyl, or carboxy. A particular phosphonic acid moiety Z is —$(CR_2)_{1-4}$-phosphonic acid, wherein R is independently hydrogen, halo, amino, or hydroxy. In an even more particular embodiment Z is $(CR_2)_{1-6}$-phosphonic acid, wherein R is independently hydrogen, halo, or hydroxy.

Z may also be substituted or unsubstituted $C_{1-10}$alkyl-O—C(O)—$C_{1-10}$alkyl. Again, when either alkyl moiety is substituted, it is in one embodiment substituted by halogen, hydroxy, alkyl, nitro, amino, haloalkyl, alkylamino, dialkylamino, acyl, or acyloxy. The $C_{1-10}$alkyl substituents are in one embodiment straight chain alkylene moieties comprising one to five carbon atoms, mono- or polysubstituted by hydroxy. Thus, in one embodiment Z is represented by —$(CR_2)_{1-6}$—O—C(O)—$(CR_2)_{1-6}$—$CHR_2$, wherein R is independently hydrogen, amino, halo, or hydroxy. In a more particular embodiment Z is —$(CHR)_{1-6}$—O—C(O)—$(CHR)_{1-6}$—$CRH_2$, wherein R is independently hydrogen or hydroxy. In one particular embodiment Z is —$CH_2$—CH(OH)—$CH_2$—O—C(O)—$(CH(OH))_4$—$CH_2OH$.

In still another embodiment Z is a straight chained $C_{3-10}$polyhydroxylated alkyl. In one particular embodiment Z is —$CH_2$—$(CHR')_{1-8}$—$CH_2R'$; wherein R' is independently hydrogen or hydroxy, and at least two, three, four, or five of R' are hydroxy. In another particular embodiment Z is —$CH_2$—$(CHR')_{1-6}$—$CH_2R'$; wherein R' is independently hydrogen or hydroxy, and at least two, three, or four of R' are hydroxy. In an even more particular embodiment Z is —$CH_2$—$(CH(OH))_3$—$CH_2OH$.

In yet another embodiment Z is —$(CR_2)_{1-10}$—COOH, or —$(CR_2)_{1-6}$—COOH, wherein R is independently hydrogen, halo, amino, or hydroxy, and wherein at least one of the R substituents is not hydrogen. In another embodiment Z is defined by —$(CH_2)_{0-6}$—$CF_2$—COOH or —$(CH_2)_{1-6}$—CH the foregoing embodiments can be selected from substituted or unsubstituted pyrolidine, imidazole, pyridine, and pyrimidine. Substituents include hydroxy, amino ($NR^1R^2$ wherein $R^1$ and $R^2$ are independently hydrogen or lower alkyl), lower alkoxy, halo, and carboxy.

Examples of species of thioketals are defined when $R_a$, $R_b$, $R_c$, and $R_d$ are t-butyl, and Z is:
(i) arabitol;
(ii) ribofuranose;
(iii) 2-hydroxy-3-propyl-D-gluconate; or
(iv) 2-hydroxypropan-3-sulfonic acid.

These compounds are represented structurally in the following table III:

TABLE III

| Compound name | Z |
|---|---|
| D-Gluconate, 2-hydroxy-3-[4-[[1-[[3,5-bis(1,1-dimethylethyl)-4-hydroxyphenyl]thio]-1-methylethyl]thio]-2,6-bis(1,1-dimethylethyl)phenoxy]propyl | |
| Propanesulfonic acid, 2-hydroxy-3-[4-[[1-[[3,5-bis(1,1-dimethylethyl)-4-hydroxyphenyl]thio]-1-methylethyl]thio]-2,6-bis(1,1-dimethylethyl)phenyl] | |
| D-Arabitol, 5-O-[4-[[1-[[3,5-bis(1,1-dimethylethyl)-4-hydroxyphenyl]thio]-1-methylethyl]thio]-2,6-bis(1,1-dimethylethyl)phenyl] | |
| D-Ribofuranose, 5-O-[4-[[1-[[3,5-bis(1,1-dimethylethyl)-4-hydroxyphenyl]thio]-1-methylethyl]thio]-2,6-bis(1,1-dimethylethyl)phenyl] | |

($NR^1R^2$)—COOH, wherein $R^1$ and $R^2$ are independently hydrogen or lower alkyl, in one embodiment hydrogen.

In another embodiment Z is —$(CR_2)_{1-6}$—X, wherein X is substituted or unsubstituted aryl, heteroaryl, or heterocycle, and R is independently hydrogen, halo, amino, or hydroxy. In another embodiment Z is —$(CHR)_{1-6}$—X, wherein X is substituted or unsubstituted aryl, heteroaryl, or heterocycle, and R is independently hydrogen or hydroxy. X in either of Other compounds are defined by formula (I) when Z is: 2-amino-3-carboxypropyl; 3-amino-4-carboxybutyl; 1,1-difluoro-1-carboxymethyl; phosphonomethyl; 1,1-difluoro-1-phosphono-methyl; 2-(2-carboxy-N-pyrrolidine)ethyl; (2H-imidazol-5-yl)methyl; 2-pyridylmethyl; 3-pyridylmethyl; and 5-pyrimidinylmethyl.

The chemical structure for Z can be represented as set forth in Table IV:

TABLE IV

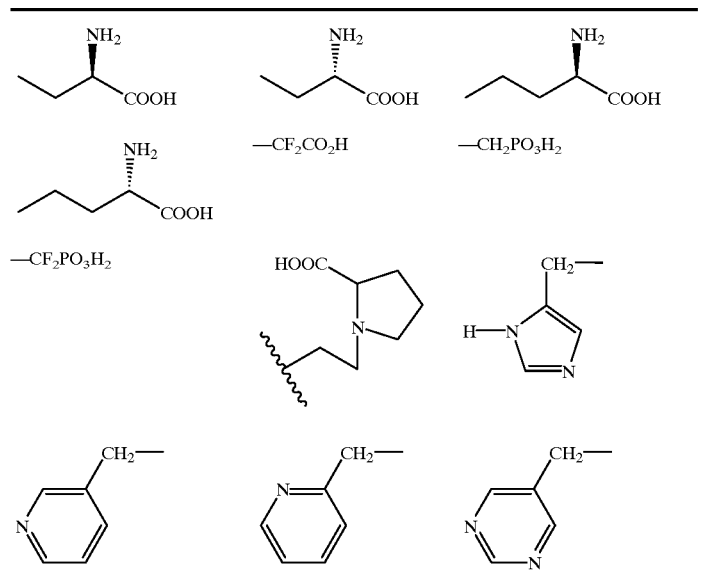

In another embodiment the invention provides compounds of formula (II), and their pharmaceutically acceptable salts:

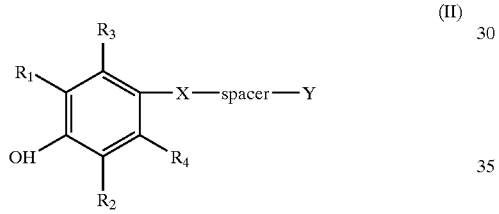

wherein:
a) X is O, S, SO, $SO_2$, $CH_2$, or NH;
b) spacer is —$(CH_2)_n$—, —$(CH_2)_n$—CO—, —$(CH_2)_n$—NH—, —$(CH_2)_n$—O—, —$(CH_2)_n$—S—, —$(CH_2O)$—, —$(OCH_2)$—, —$(SCH_2)$—, —$(CH_2S)$—, —(aryl-O)—, —(O-aryl)—, —(alkyl-O)—, —(O-alkyl)—; —O—C(O)—$(CH_2)_n$, —$(CH_2)_n$—C(O)—O—, S—C(S)—$(CH_2)$n, —$(CH_2)_n$—C(S)—S—, —C(S)—;
c) n is 0, 1, 2, 3, 4, 5, 6, 7, 8, 9, or 10;
d) $R^1$ and $R^2$ are independently straight chained, branched, or cyclic alkyl which may be substituted, aryl, substituted aryl, heteroaryl, substituted heteroaryl, alkaryl, or aralkyl;
e) $R^3$ and $R^4$ are independently any group that does not otherwise adversely affect the desired properties of the molecule, including H, halogen, or $R^1$; and
f) Y is aryl or heteroaryl monosubstituted by —C(O)$NR_5R_6$, wherein $R_5$ and $R_6$ are independently hydrogen or alkyl.

The compounds are optionally substituted by halogen, alkyl, nitro, amino, amido, cyano, haloalkyl, alkylamino, O-alkyl, S-alkyl, OH, SH, dialkylamino, acyl, or carboxy.

In one particular embodiment —X-spacer- is —S—$CH_2$—, $R^1$ and $R^2$ are substituted or unsubstituted branched alkyl, $R^3$ and $R^4$ are hydrogen or lower alkyl; and Y is aryl or heteroaryl monosubstituted by —C(O)$NR_5R_6$, wherein $R_5$ and $R_6$ are independently hydrogen or lower alkyl.

In another particular embodiment —X-spacer- is —S—$CH_2$—, $R^1$ and $R^2$ are t-butyl, $R^3$ and $R^4$ are hydrogen; and Y is aryl or heteroaryl monosubstituted by —C(O)$NR_5R_6$, wherein $R_5$ and $R_6$ are independently hydrogen or alkyl.

In an even more particular embodiment —X-spacer- is —S—$CH_2$—, $R^1$ and $R^2$ are t-butyl, $R^3$ and $R^4$ are hydrogen, and Y is 4'-(N,N-dimethylaminocarbonyl)benzyl or 4'-(N,N-diethylaminocarbonyl)benzyl. These compounds are represented structurally in the following table V.

TABLE V

| Structure | Name |
| --- | --- |
| 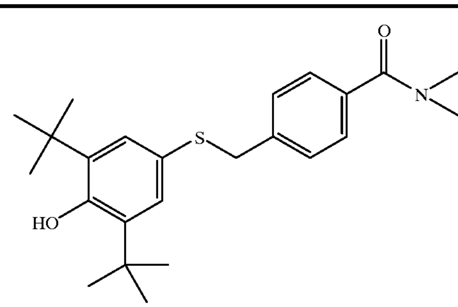 | 2,6-Di-tert-butyl-[4'-(N,N-dimethylaminocarbonyl)benzyl]thiophenol |

TABLE V-continued

| Structure | Name |
|---|---|
| 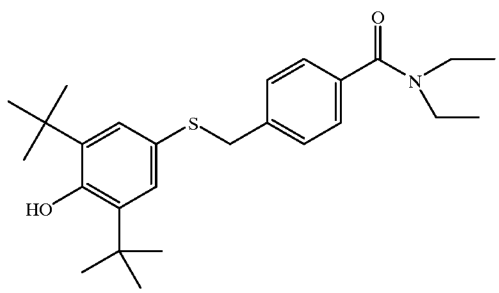 | 2,6-Di-tert-butyl-[4'-(N,N-diethylaminocarbonyl)benzyl]thiophenol |

In one embodiment the compounds of formulas (I) and (II) display VCAM-1 $IC_{50}$ inhibition concentrations of less than about 25, 15, 10, or 5 µM, or $LD_{50}$ concentrations greater than twice, thrice, five times, or ten times the VCAM-1 $IC_{50}$ concentration.

In another embodiment the compounds of formulas (I) and (II) display ApoB/HepG2 $IC_{50}$ inhibition concentrations of less than about 25, 15, or 10 µM, or $LD_{50}$ concentrations greater than twice, thrice, five times, or ten times the ApoB/HepG2 $IC_{50}$ inhibition concentration.

In another aspect the invention provides pharmaceutical compositions for the treatment of diseases or disorders mediated by VCAM-1 wherein such compositions comprise a thioketal or thioether of the formula (I) or (II) or a pharmaceutically acceptable salt thereof and a pharmaceutically acceptable carrier. Exemplary pharmaceutical compositions and pharmaceutically acceptable carriers are set forth below in "Pharmaceutical Compositions and Modes of Administration."

Pharmaceutically Acceptable Salts

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enatiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chrial catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Definitions

The term alkyl, as used herein, unless otherwise specified, refers to a saturated straight, branched, or cyclic, primary, secondary, or tertiary hydrocarbon, including but not limited to those of $C_1$ to $C_{10}$, and preferably $C_1$-$C_6$, including methyl, (cyclopropyl)methyl, (cyclobutyl)methyl, (cyclopentyl)methyl, ethyl, 1-cyclopropylethyl, 2-cyclopropylethyl, 1-cyclobutylethyl, 2-cyclobutylethyl, propyl, isopropyl, 1-(cyclopropyl)propyl, 2-(cyclopropyl) propyl, 3-(cyclopropyl)propyl, cyclopropyl, methylcyclopropyl, 2,2-dimethylcyclopropyl, 1,2-dimethylcyclopropyl, ethylcyclopropyl, propylcyclopropyl, 1-ethyl-1-methylcyclopropyl, 1-ethyl-2-methylcyclopropyl, 1,1,2-trimethylcyclopropyl, 1,2,3-trimethylcyclopropyl, butyl, isobutyl, t-butyl, sec-butyl, 2,2-dimethylbutyl, 2,3-dimethylbutyl, cyclobutyl, methylcyclobutyl, 1,1-dimethylcyclobutyl, 1,2-dimethylcyclobutyl, 1,3-dimethylcyclobutyl, ethylcyclobutyl, pentyl, isopentyl, neopentyl, 2-methylpentyl, 3-methylpentyl, cyclopentyl, methylcyclopentyl, spiropentyl, methylspiropentyl, hexyl, isohexyl and cyclohexyl. The alkyl group can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "alditol," as referred to herein, and unless otherwise specified, refers to a carbohydrate in which the aldehyde or ketone group has been reduced to an alcohol moiety. The alditols of the present invention can also be optionally substituted or deoxygenated at one or more positions. Exemplary substituents include hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate, phosphonic acid, phosphonate, or any other viable functional group that does not inhibit the pharmacological activity of this compound. Particular exemplary substituents include amine and halo, particularly fluorine. The substituent or alditol can be either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The alditol may comprise 3, 4, 5, 6, or 7 carbons. Examples of useful alditols are those derived from reduction of monosaccharides, including specifically those derived from the reduction of pyranose and furanose sugars.

The term "carbohydrate," as referred to herein, and unless otherwise specified, refers to a compound of carbon, hydrogen, and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment the carbohydrates are monosaccharides. In another embodiment the carbohydrates are pyranose and furanose sugars.

Non limiting examples of pyranose and furanose sugars include threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine.

The carbohydrate can be optionally deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate, phosphonic acid, phosphonate, or any other viable functional group that does not inhibit the pharmacological activity of this compound. Particular exemplary substituents include amine and halo, particularly fluorine. The substituent or carbohydrate can be either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_6$ saturated straight, branched, or if appropriate, a cyclic (for example, cyclopropyl) alkyl group.

The term "—$(CH_2)_n$—" represents a saturated alkylidene radical of straight chain configuration. The term "n" can be any whole integer, including 0, 1, 2, 3, 4, 5, 6, 7, 8, 9, or 10. The moiety "—$(CH_2)_n$—" thus represents a bond (i.e., when n=0), methylene, 1,2-ethylene or 1,3-propylene, etc.

The term aryl, as used herein, and unless otherwise specified, refers to phenyl, biphenyl, or naphthyl, and in one embodiment phenyl. The aryl group can be optionally substituted with one or more moieties selected from the group consisting of hydroxyl, acyl, amino, halo, alkylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term heteroaryl or heteroaromatic, as used herein, refers to an aromatic or unsaturated cyclic moiety that includes at least one sulfur, oxygen, nitrogen or phosphorus in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl. The heteroaryl group can be optionally substituted with one or more moieties selected from the group consisting of hydroxyl, acyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al, "Protective Groups in Organic Synthesis," John Wiley and Sons, Second Edition, 1991, hereby incorporated by reference.

The term heterocyclic refers to a nonaromatic cyclic group that can include alkyl moieties which may be substituted, and wherein there is at least one heteroatom, such as oxygen, sulfur, nitrogen, or phosphorus in the ring. Nonlimiting examples are morpholine, piperidine, piperazine, pyrrolidine, azetidine, and tetrahydrofuran. The heterocyclic group can be optionally substituted with one or more moieties selected from the group consisting of hydroxyl, acyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term aralkyl, as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. The aralkyl or alkaryl group can be optionally substituted with one or more moieties selected from the group consisting of hydroxyl, acyl, amino, alkylamino, arylamino, alkoxy, aryloxy, nitro, cyano, sulfonic acid, sulfate, phophonic acid, phosphate, or phosphonate, either unprotected, or protected as necessary, as known to those skilled in the art, for example, as taught in Greene, et al, "Protective Groups in Organic Synthesis," John Wiley and Sons, Second Edition, 1991, hereby incorporated by reference.

The term halo, as used herein, includes chloro, bromo, iodo, and fluoro.

The term alkoxy, as used herein, and unless otherwise specified, refers to a moiety of the structure —O-alkyl, wherein alkyl is as defined above.

The term acyl, as used herein, refers to a group of the formula C(O)R', wherein R' is an alkyl, aryl, alkaryl or aralkyl group, or substituted alkyl, aryl, aralkyl or alkaryl, wherein these groups are as defined above.

The term amino includes primary, secondary, and tertiary amines. An amino moiety can be represented generally by the formula $NR^1R^2$, wherein $R^1$ and $R^2$ are independently hydrogen or substituted or unsubstituted lower alkyl.

The term pharmaceutically acceptable salts or complexes refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —$NR^+A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The term "allograft" means the transfer of tissue between two genetically dissimilar individuals of the same species, such as a tissue transplant between two humans who are not identical twins. Examples of allografted organs include lung, heart, kidney, liver, pancreas and bone marrow.

Methods of Treatment

In another aspect the invention provides a method for treating a disease or disorder mediated by VCAM-1 comprising administering to a patient a VCAM-1 inhibiting effective amount of a compound of formula (I) or (II) or a pharmaceutically acceptable salt thereof. Exemplary effective amounts and modes of administration are set forth below in "Pharmaceutical Compositions and Modes of Administration."

VCAM-1 is implicated in a number of disorders which can be treated using the compounds of the present invention, including inflammatory disorders, cardiovascular diseases, occular diseases, autoimmune diseases, neurological disorders, and cancer.

Exemplary inflammatory disorders include but are not limited to rheumatoid arthritis, osteoarthritis, inflammatory bowel disease, Crohn's disease, asthma, allergic rhinitis, sinusitis, chronic obstructive pulmonary disease (COPD), dermatitis, psoriasis, cystic fibrosis, multiple sclerosis, vasculitis, and organ transplant rejection (allograft rejection).

Exemplary cardiovascular diseases include but are not limited to atherosclerosis, post-angioplasty restenosis, coronary artery disease, angina, small artery disease, diabetes mellitus, diabetic nephropathy, and diabetic retinopathy.

Exemplary occular diseases include but are not limited to uveitis and macular degeneration.

Exemplary autoimmune diseases include but are not limited to systemic lupus erythematosus, autoimmune type-1 diabetes, and graft versus host disease.

Systemic lupus erythematotus, or SLE, attacks multiple systems in the body including the skin, joints, lungs, blood, blood vessels, heart, kidneys, liver, brain and the nervous system. The method can be practiced to treat any of the symptoms of SME, including achy joints (arthralgia), fever arthritis, prolonged or extreme fatigue, skin rashes, anemia, chest pains (pleurisy), butterfly-shaped rashes across the cheeks and nose, weight gain, high blood pressure, dark urine, swelling around the eyes, legs, ankles, or fingers, photosensitivity, hair loss, abnormal blood clotting problems, Raynaud's phenomenon (fingers turning white and/or blue in the cold), seizures and mouth or nose ulcers Type 1 autoimmune diabetes is another autoimmune disease that can be treated according to the methods of the present invention. The methods of this invention can be used to treat any of the symptoms of type-1 diabetes including frequent urination, unusual thirst, extreme hunger, unusual weight loss, extreme fatigue and irritability.

Exemplary neurological diseases include but are not limited to Alzheimer's disease, Parkinson's disease, and amyotrophic lateral sclerosis (ALS).

Exemplary cancers include but are not limited to tumor metastasis and angiogenesis.

As mentioned above, the compounds of the present invention also treat hypercholesterolemia and hyperlipidemia. Thus, in another aspect the invention provides a method and composition for treating hypercholesterolemia in a patient in need thereof comprising administering to said patient an effective amount of a compound of formula (I) or (II) or a pharmaceutically acceptable salt thereof. In still another aspect the invention provides a method and composition for treating hyperlipidemia in a patient in need thereof comprising administering to said patient an effective amount of a compound of formula (1) or (II) or a pharmaceutically acceptable salt thereof.

The active compound can be administered in conjunction with other medications used in the treatment of cardiovascular disease, including platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compound can also be administered in combination with nonsteroidal antiinflammatories such as ibuprofen, indomethacin, fenoprofen, mefenamic acid, flufenamic acid, and sulindac. The compound can also be administered in combination with a COX-2 inhibitor, for example, celecoxib. The compound can also be administered with a corticosteriod. The compound can also be administered in combination with a TNF-α modulating agent, for example, etanercept or infliximab.

EXPERIMENTALS

Example 1

Thioketal Synthetic Methods

The thioketal compounds of formula (I) wherein Z forms an ether group can be prepared by known procedures and techniques, or routine modifications thereof. General procedures for preparing compounds of formula (I) wherein Z forms an ether group are set forth in General Procedures A and B, wherein all substituents, unless otherwise indicated, are previously defined.

General Procedure A

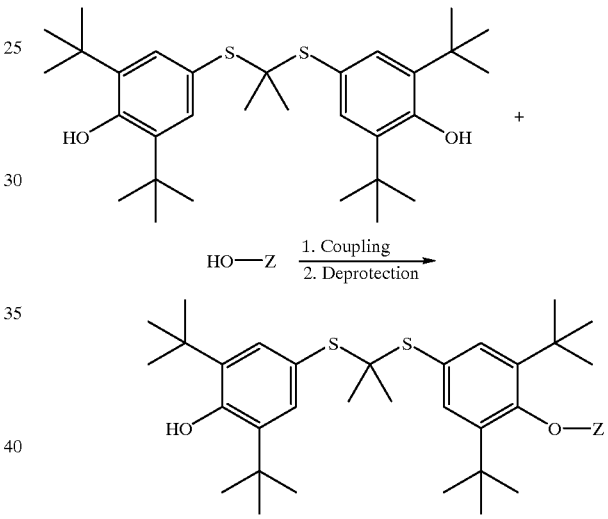

Compounds of the present invention can be readily prepared by someone skilled in the art of organic synthesis using a standard ether coupling procedure known as the Mitsunobu reaction (Hughes, D. L. Org. Prep. Proced. Int., 28, 127–64 (1996)). For example, to a solution of probucol in a suitable aprotic solvent such as tetrahydrofuran (THF) are added triphenylphosphine, diethyl azodicarboxylate, and an appropriate alcohol moiety optionally containing the additional substituents described above for Z. The resultant mixture is stirred under nitrogen at reflux for 2 to 8 hours and then evaporated. Chromatography on silica gel gives the desired ether product. Alternatively, one skilled in the art can replace the triphenylphosphine reagent with other suitable phosphine reagents, including but not limited to tributylphosphine and polymer-supported triphenylphosphine. One may also use dimethyl azidodicarboxylated in place of diethyl azidodicarboxylate. Since Z may also contain one or more alcohol, amine, carboxylate, phosphonate, or thiol substituents that may participate in the reaction, one normally skilled in the art may choose to protect these substituent groups prior to the reaction. Compounds of the present invention include the resulting protected intermediates. Alternatively, one skilled in the art can selectively remove these protecting groups using well established and known procedures to give the desired ether products containing one or more deprotected alcohol, amine, carboxylate, phosphonate or thiol substituents in Z. In one embodiment, the alcohol group included in Z above is a primary alcohol.

General Procedure B

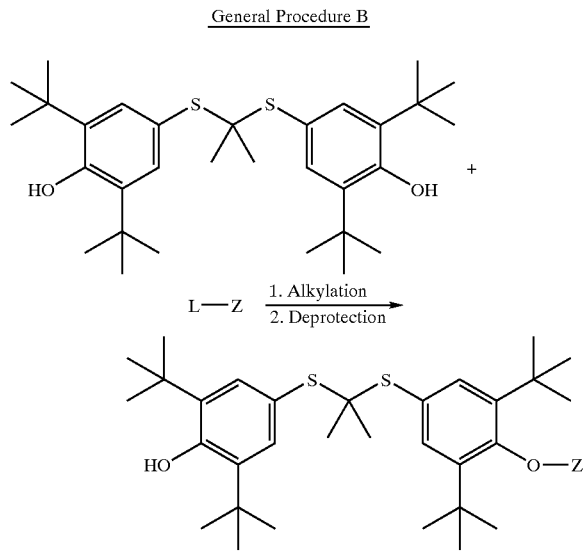

Alternatively, compounds of the present invention can be readily prepared by someone skilled in the art of organic synthesis using a standard alkylation reaction of the phenol. For example, to a solution of probucol in a suitable aprotic solvent such as tetrahydrofuran (THF) or dimethylformamide are added a strong base such as sodium hydride or potassium hydroxide or a tertiary amine base such as triethylamine, dimethyl aminopyridine, pyridine or diisopropylethylamine. Then an appropriate electrophile containing the Z-group attached to an appropriate leaving group, L, is added. Examples of suitable L-leaving groups include halogens such as chloride, bromide or iodide and alcohol derivatives such as mesylates, tosylates and triflates. The Z group may optionally contain additional substituents as described above for Z. The resultant mixture is stirred under nitrogen at reflux for 2 to 8 hours and then evaporated. Chromatography on silica gel gives the desired ether product. Since Z may also contain one or more alcohol, amine, carboxylate, phosphonate, or thiol substituents that may participate in the reaction, one normally skilled in the art may choose to protect these substituent groups prior to the reaction. Compounds of the present invention include the resulting protected intermediates. Alternatively, one skilled in the art can selectively remove these protecting groups using well established and known procedures to give the desired ether products containing one or more deprotected alcohol, amine, carboxylate, phosphonate, or thiol substituents in Z.

General Procedure C

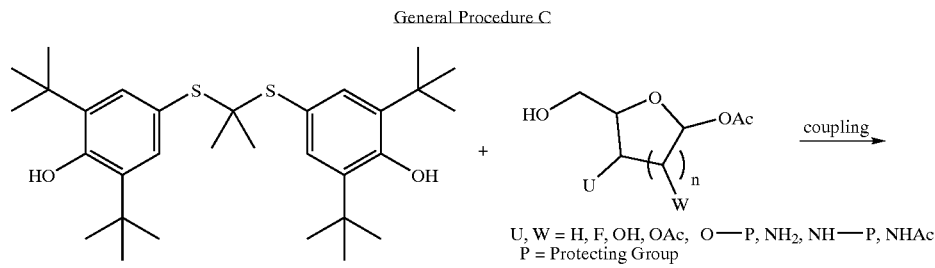

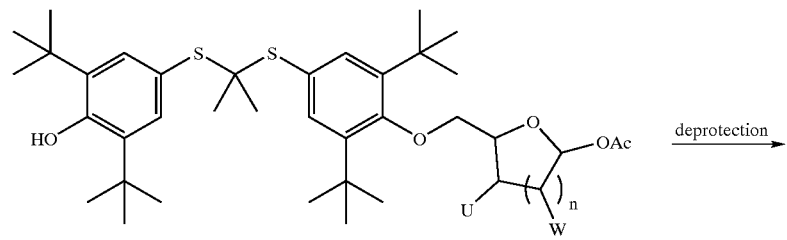

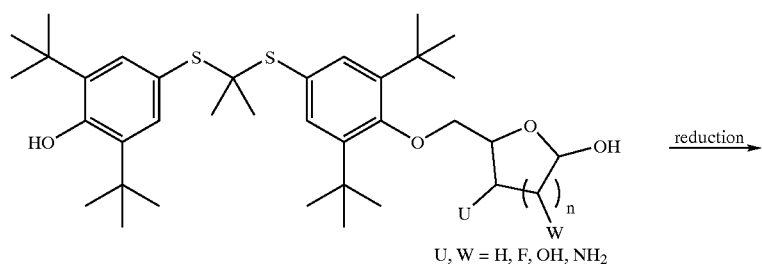

-continued

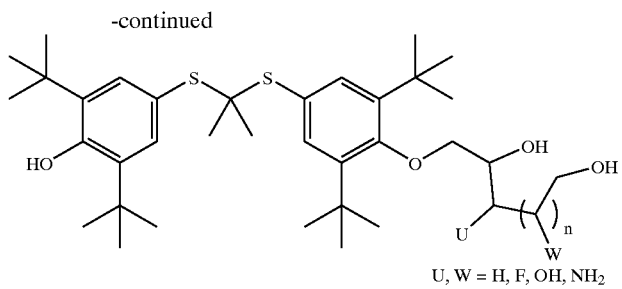

U, W = H, F, OH, NH$_2$

Compounds of the present invention can also be readily prepared by someone skilled in the art of organic synthesis using a standard ether coupling procedure known as the Mitsunobu reaction. For example, to a solution of probucol in a suitable aprotic solvent such as tetrahydrofuran (THF) are added triphenylphosphine, diethyl azodicarboxylate, and an appropriate carbohydrate, in one embodiment containing a primary alcohol moiety, and optionally containing additional halogen or amine substituents described above for Z. The resultant mixture is stirred under nitrogen at reflux for 2 to 8 hours and then evaporated. Chromatography on silica gel gives the desired ether coupling product. Alternatively, one skilled in the art can replace the triphenylphosphine reagent with other suitable phosphine reagents, including but not limited to tributylphosphine and polymer-supported triphenylphosphine. One may also use dimethyl azidodicarboxylated in place of diethyl azidodicarboxylate. Since the carbohydrate may also contain one or more alcohol or amine substituents that may participate in the reaction, one normally skilled in the art may choose to protect these substituent groups prior to the reaction. Preferable protecting groups include acetates or ketals to protect alcohols and amides to protect amines. Compounds of the present invention include the resulting protected intermediates. One skilled in the art can selectively remove these protecting groups using well established and known procedures to give the desired deprotected ether products. Preferable deprotection reagents for acetate groups include but are not limited to an inorganic base such as potassium carbonate in a protic organic solvent such as methanol or ethanol. For acetyl-protected carbohydrates, the product is dissolved in methanol and potassium carbonate is added. The reaction mixture is stirred for up to 8 hours with or without heating. When the reaction is complete the product is extracted with dichloromethane from brine and purified by chromatography on silica gel to give the desired deprotected probucol-carbohydrate derivatives, as shown in Table I. Preferable deprotection reagents for ketal groups include but are not limited to inorganic acids such as aqueous hydrochloric acid in a suitable organic solvent such as methylene chloride.

The above deprotected probucol-carbohydrate ether compounds can also be dissolved in an organic solvent such as THF and a suitable reducing agent such as lithium aluminum hydride is added. The reaction mixture is stirred for up to 8 hours with or without heating. Upon quenching, the product is extracted with dichloromethane from brine and purified by chromatography on silica gel to give the reduced functionalized probucol-polyol derivatives, as shown in Table II.

The chemical reactions described above are generally disclosed in terms of their broadest applications to the preparation of the compounds of the present invention. Occasionally, the reactions may not be applicable as described to each compound included within the disclosed scope. The compounds for which this occurs will be readily recognized by those skilled in the art. In all such cases, either the reactions can successfully performed by conventional modifications recognized by those skilled in the art, e.g., by appropriate protection and deprotection of interfering groups, by changing to alternative conventional solvents or reagents, by routine modification of reaction conditions and the like, or other conventional reactions will be applicable to the preparation of the corresponding compounds of the present invention. In all preparative methods, all starting materials are known or readily prepared from known starting materials.

Example 2

D-arabitol, 5-O-[4-[[1-[[3,5-bis(1,1-dimethylethyl)-4-hydroxyphenyl]thio]-1-methylethyl]thio]-2,6-bis(1,1-dimethylethyl)phenyl] and D-ribose, 5-O-[4-[[1-[[3,5-bis(1,1-dimethylethyl)-4-hydroxyphenyl]thio]-1-methylethyl]thio]-2,6-bis(1,1-dimethylethyl)phenyl]

Probucol (21 g, 40.4 mmol) was dissolved in THF (250 mL), and treated with the 2-3-dimethylethyl acetal of D-ribolactone (33.8 mmol, 6.9 g), triphenylphosphine (10.6 g, 40.4 mmol), and diethylazo-dicarboxylate (6.4 mL, 40.4 mmol). The reaction was refluxed for 3 h followed by evaporation of the solvent and chromatography (ether/hexane 20%-40%) to give 3.2 g (13.5%) of the intermediate lactone. The lactone (4.36 g) was dissolved in 100 ml of methanol, 10 ml of acetic acid and 2 mL of water. The reaction was refluxed 72 hours. The reaction solvents were evaporated and the resulting oil dissolved in methylene chloride, washed with 1 N NaOH, and water. The organic layer was dried over sodium sulfate and concentrated to yield 4 g of a white fluffy solid. The white fluffy solid was dissolved in 50 mL of THF and treated with 25 mL of 1N NaOH and stirred overnight at RT. The solvent was evaporated and the residue dissolved in methylene chloride and treated with 1N HCl to pH=7. The water layer was extracted with methylene chloride and then washed with water . The organic layer was dried over sodium sulfate, filtered, and concentrated to dryness to give 4.1 g of light green syrup. The light green syrup was dissolved in 150 mL of THF and 20 mL of 1M lithium aluminum hydride in ether was added at RT and stirred for 4 hours. The reaction was quenched with 50 mL of sat. sodium sulfate and stirred overnight. The organics were extracted with ether, dried over sodium sulfate and concentrated to dryness. The reaction products were purified by column chromatography (50% ether/hex to 100% ether). Three reaction products were separated and identified: 980 mg lactone, 600 mg lactol (15% yield; D-ribose, 5-O-[4-[[1-[[3,5-bis(1,1-dimethylethyl)-4-hydroxyphenyl]thio]-1-methylethyl]thio]-2,6-bis(1,1-dimethylethyl)phenyl]), and 600 mg of alcohol (15% yield; D-arabitol, 5-O-[4-[[1-[[3,5-bis(1,1-dimethylethyl)-4- hydroxyphenyl]thio]-1-methylethyl]thio]-2,6-bis(1,1-dimethylethyl)phenyl]).

Example 3

D-Gluconate, 2-hydroxy-3-[4-[[1-[[3,5-bis(1,1-dimethylethyl)-4-hydroxyphenyl]thio]-1-methylethyl]thio]-2,6-bis(1,1-dimethylethyl)phenoxy]propyl 15.5 mmol (8.01 g) of probucol was stirred in dry THF (150 mL) at 0° C. Glycidol (31.1 mmol; 2.15 mL) was added, followed by triphenylphosphine (31.1 mmol; 8.13 g) and diethyl azodicarboxylate (31.1 mmol; 4.9 mL). The brown mixture was stirred at 0° C. for 15 min. then warmed to room temperature. The mixture was heated to reflux and stirred for 3 days. The mixture was cooled to room temperature, and solvent was removed by rotary evaporation to give a crude oil. Purification of the oil by column chromatography (SiO$_2$; 4:1 hexanes-CH$_2$Cl$_2$ then 2:1 hexanes-CH$_2$Cl$_2$) gave 2.9 g of the glycidol mono-ether of probucol as a yellow solid.

The glycidol mono-ether of probucol (0.61 mmol; 350.7 mg) was dissolved in 15 mL of DMF at room temperature. The resulting solution was treated with gluconic acid (1.5 mmol; 0.24 mL) then stirred at room temperature for 24 hours. The mixture was then diluted with ethyl acetate and washed with water. The organic phase was washed with brine. Solvent was removed by rotary evaporation to give an oil. Purification of the oil by radial chromatography (SiO$_2$) using CH$_2$Cl$_2$ followed by 4% MeOH—CH$_2$Cl$_2$ then 9% MeOH—CH$_2$Cl$_2$ to give the product contaminated with DMF. DMF was removed by dissolving the product in Et$_2$O and washing with water (3×50 mL). The ether phase was dried over sodium sulfate. Filtration and solvent removal (rotary evaporation) gave 60.6 mg of a beige foam.

The foregoing procedures can similarly be used to prepare compounds of formula (I) wherein Z is defined by the following structures in tables VI, VII, and VIII:

TABLE VI

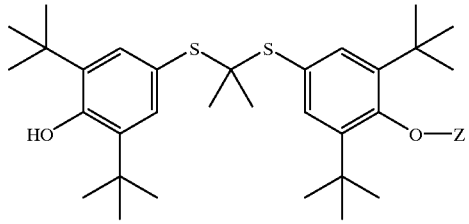

| Example Number | Z |
|---|---|
| 3a | 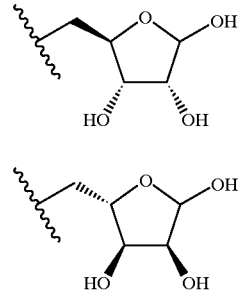 |
| 3b | 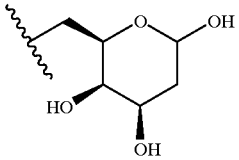 |

TABLE VI-continued

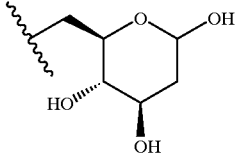

| Example Number | Z |
|---|---|
| 3c | 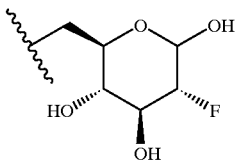 |
| 3d | 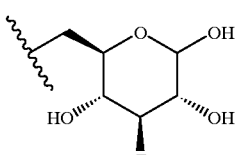 |
| 3e | 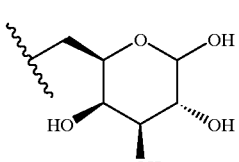 |
| 3f | 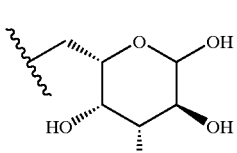 |
| 3g | 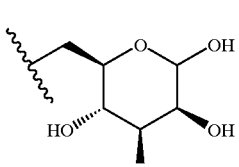 |
| 3h |  |
| 3i |  |

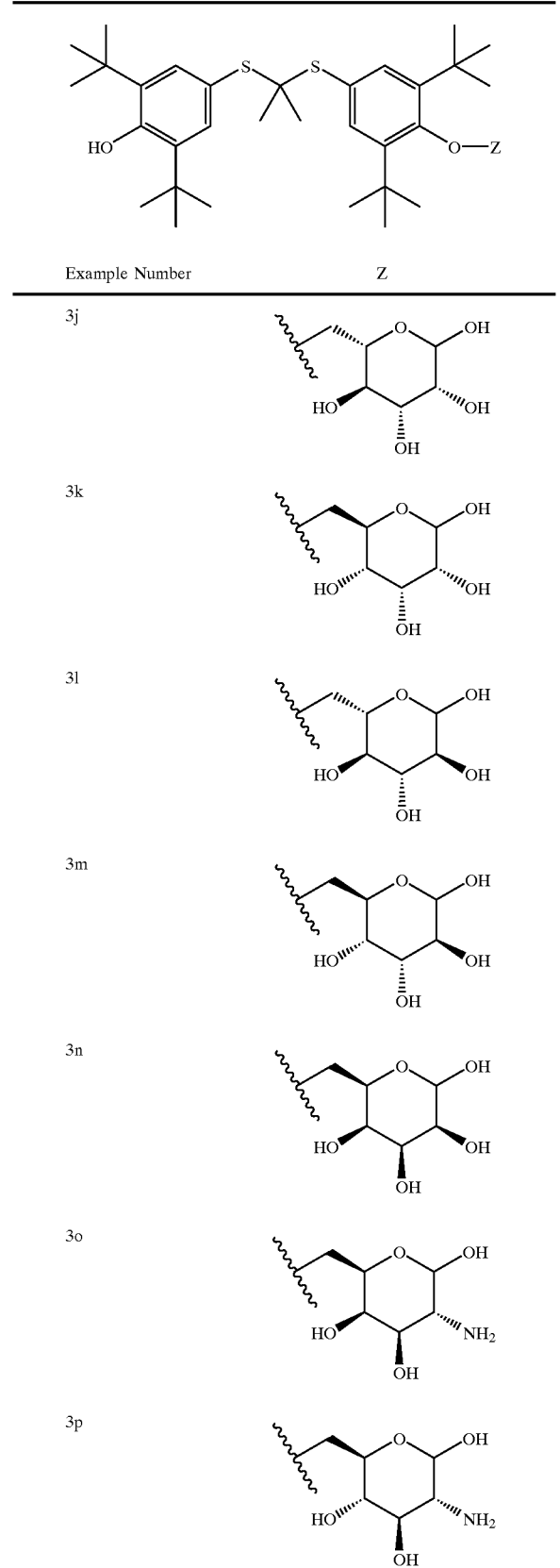
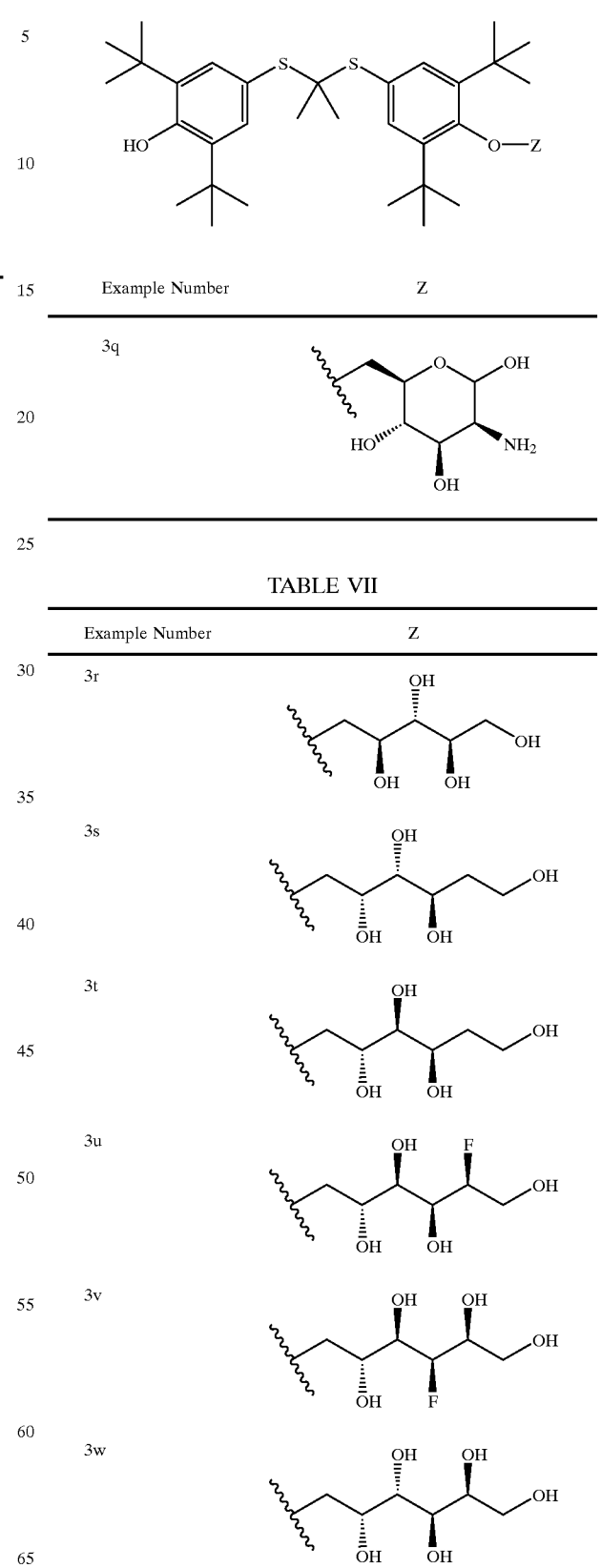

TABLE VII-continued
| Example Number | Z |
|---|---|
| 3x | 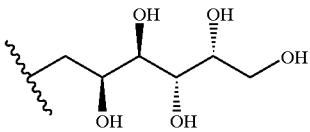 |
| 3y | 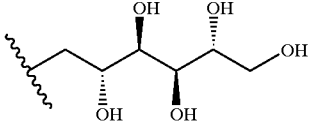 |
| 3z | 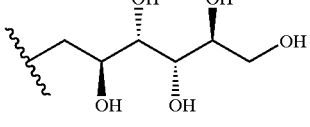 |
| 3a' | 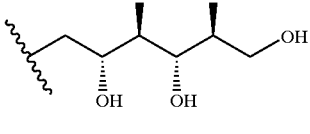 |
| 3b' | 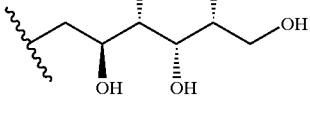 |
| 3c' | 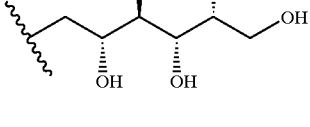 |
| 3d' | 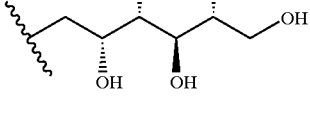 |
| 3e' | 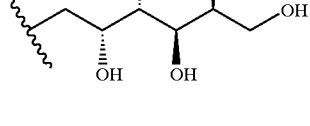 |
| 3f' | 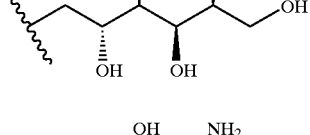 |
| 3g' | 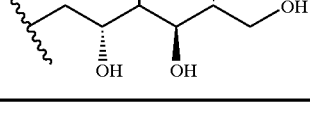 |
TABLE VIII
| Example Number | Z |
|---|---|
| 3h' | 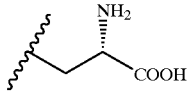 |
| 3i' | 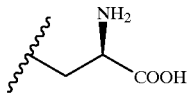 |
| 3j' | 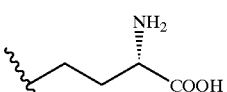 |
| 3k' | 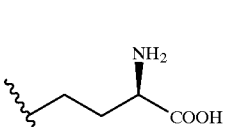 |
| 3l' | 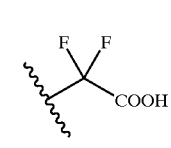 |
| 3m' | 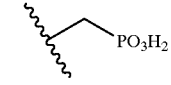 |
| 3n' | 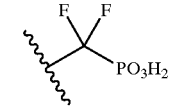 |
| 3o' | 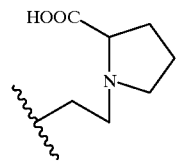 |
| 3p' | 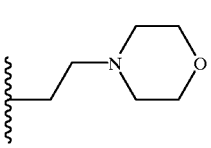 |
| 3q' | 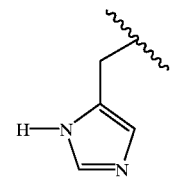 |

TABLE VIII-continued

| Example Number | Z |
|---|---|
| 3r' |  |
| 3s' | 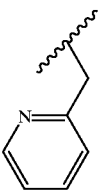 |
| 3t' | 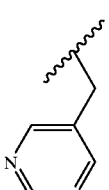 |

Example 4

Thioether Synthetic Methods

The thioethers of formula (II) can be prepared by utilizing known procedures and techniques, or routine modifications thereof. See, for example, the synthetic methods disclosed in PCT/US98/09781 published as WO 98/51662. A general synthetic method for preparing compounds of formula (II) is set forth in General Procedure C, wherein all substituents, unless otherwise indicated, are previously defined.

General Procedure C

The synthesis of the starting thiol, 4-mercapto-2,6-di-t-butylphenol, is described in the literature (U.S. Pat. No. 3,129,262 to Laufer, incorporated herein by reference in its entirety). The starting alkyl halides are commercially available or made from commercially available starting materials by methods known to one of ordinary skill in the art.

A quantity of the 4-mercapto-2,6-di-t-butylphenol is dissolved in ethanol to make a 0.5 M solution and treated with 1.2 equivalents of sodium hydroxide (5 N aqueous solution). After 5 minutes 1.2 equivalents of alkyl halide are added and the reaction mixture stirred at room temperature for 24 hours. The reaction is quenched with 1 N HCl to pH 7, diluted with water, extracted with ether and dried over magnesium sulfate. The product is purified by silica gel chromatography.

Starting materials for use in the general synthetic procedure outlined in General Procedural C are readily available to one of ordinary skill in the art. For example, certain phenol starting materials for various compounds of formula (I), such as 2,6-di-tertiarybutyl-4-mercaptophenol, are described in U.S. Pat. No. 3,576,883, U.S. Pat. No. 3,952,064, U.S. Pat. No. 3,479,407 and in Japanese Patent Application 73-28425.

In general, a phenol of structure (II) can be prepared by dissolving the appropriate 2,6-dialkyl-4-thiophenol (or suitably protected derivatives) in alcohol, in one embodiment in ethanol, followed by addition of a halogenated aryl compound.

The starting material, a 2,6-dialkyl-substituted thiophenol, may be protected by any of the many protecting groups known to one of ordinary skill in the art. Examples of suitable phenol protecting groups are ethers, such as methoxymethyl, 2-methoxyethoxymethyl, tetrahydropyranyl, t-butyl and benzyl; silyl ethers, such as trimethylsilyl and 1-butyldimethylsilyl; esters, such as acetate and benzoate; carbonates, such as methylcarbonate and benzyl carbonate; as well as sulfonates, such as methane sulfonate and toluene sulfonate.

Example 5

2,6-Di-tert-butyl-[4'-(N,N-dimethylaminocarbonyl) benzyl]thiophenol 2.21 mol (382.5 mg) of 4-(chloromethyl)benzoyl chloride (Aldrich) in 3 mL of dry methylene chloride was stirred and treated with 2.22 mmol (0.23 mL) of dimethylamine (Aldrich) followed by 2.22 mmol (0.31 mL) of dry triethylamine. The cloudy mixture was stirred overnight.

The reaction as quenched with water and diethyl ether. The aqueous layer was extracted with 2×3 mL of diethyl ether. The combined organic layers were dried over magnesium sulfate, filtered and then concentrated by rotary evaporation to give 370 mg (74% yield) of a pale yellow solid.

0.63 mmol (149 mg) of 3,5 di-tertbutyl-4-hydroxythiophenol in 2 moL of ethanol was stirred and treated with 0.63 mmol (142 mg) of N,N-dimethyl-(4-chloromethyl)benzamide and 0.65 mmol (0.13 mL of 5N NaOH. The mixture was stirred overnight.

The reaction mixture was quenched with water/ethyl acetate. The aqueous layer was extracted with 2×3 mL of ethyl acetate. The organic phases were combined, dried over magnesium sulfate, filtered and concentrated by rotary evaporation. Purification by preparative TLC in 4:1 hexane-ethanol gave 150 of product (56% yield).

Example 6

2,6-Di-tert-butyl-[4'-(N,N-diethylaminocarbonyl) benzyl]thiophenol

Same as Example 3, but substitute diethylamine for dimethylamine.

The following examples illustrate the use of thioketals and thioethers according to the present invention. These examples are illustrative only and are not intended to limit the scope of the invention in any way.

Example 7

(Lipid Screen & IC$_{50}$ Determination Protocol)

Preparation of HEPG2:

HEPG2 cell was started in 10 ml of MEM, 10% FBS, 1 mM Sodium Pyruvate. The cells were incubated in a tissue culture incubator. The cells were split into 4×96-wells plate in MEM, 10% FBS, 1 mM Sodium Pyruvate and allowed to grow to about 50% confluency and then removed.

Day 1 Treatment:

The cells were treated with the desired concentration of compounds in 100 µl DMEM, 1% RSA for 24 hours. The compounds are dissolved in DMSO. For $IC_{50}$, the range of concentration is 10 uM-40 uM, with each concentration being done in triples.

On the same day, 4×96-wells NuncImmunoSorb plate is coated with 100 µl of mouse anti-human ApoB monoclonal 1D1 (1:1000 dilution in 1×PBS, pH 7.4). The coating is allowed to stand overnight.

Day 2 ApoB ELISA:

The coated plate is washed 3 times with 1×PBS, pH 7.4, –0.05% Tween 20. 100 µl of the standards is added to the selected wells. ApoB standards are prepared at 6.25, 3.12, 1.56, 0.78, 0.39 ng, and each concentration is done in triplicates.

For samples:

90 µl of 1×PBS, pH 7.4, –0.05% Tween 20 is added to each well corresponding to the sample. 10 µl of media is transferred from the treated HEPG2 plates to the ApoB ELISA plate. The plate is incubated at room temperature for 2 hours, rocking gently.

Wash the coated plate 3× with 1×PBS, pH 7.4, –0.05% Tween 20. Add 100µl of sheep anti-human ApoB polyclonal from Boehringer Mannheim. (1:2000 dilution in 1×PBS, pH 7.4, –0.05% Tween 20). Incubate at room temperature for 1 hour, rocking gently. Wash the coated plate 3× with 1×PBS, pH 7.4, –0.05% Tween 20. Add 100 µl of rabbit anti-sheep IgG (1:2000 dilution in 1×PBS, pH 7.4, –0.05% Tween 20). Incubate at room temperature for 1 hour, rocking gently. Wash the coated plate 3× with 1×PBS, pH 7.4, –0.05% Tween 20. Add 100 µl of substrate (10 ml of distilled water, 100 µl of TMB (10 mg/ml), and 1 µl of hydrogen peroxide). Allow color to emerge and stop reaction with 25 ul of 8N sulfuric acid. Wells are read with MicroPlate Reader @450 nM. Graph accumulation of ApoB in media as a percentage of control for each sample and their concentration. A determination of $IC_{50}$ is obtained from the graph. Data for relevant examples are summarized in Table 9.

Example 8

VCAM-1 Assay

The VCAM-1 assay is an enzyme immunoassay to detect tumor necrosis factor alpha (TNF-alpha) induced Vascular Cell Adhesion Molecule (VCAM-1) expression in endothelial cells.

Methods

Cell Culture

Human aortic endothelial cells (HAEC) were purchased from Clonetics and maintained in EGM media (Clonetics) supplemented with 5% fetal bovine serum (FBS). In a typical experiment, cells were seeded in 96-well plates. The next day cells were stimulated with TNF-alpha (1 ng/ml) purchased from Boehringer Mannheim in the presence or absence of compounds dissolved in dimethylsulphoxide (DMSO). To establish a dose curve for each compound, four concentrations in 2 fold increments were used. Cells were exposed to TNF-α and compounds for approximately 16 hours. The next day, cells were examined under microscope to score for visual signs of toxicity.

Immunoassay

Media was discarded and the cells were washed once with Hanks buffered saline solution (HBSS)/phosphate buffered solution (PBS) 91:1). Primary mouse monoclonal antibody against VCAM-1 purchased from Southern Biotechnology Associates (0.25 g/ml in HBSS/PBS+5% FBS) was added and incubated at 37° C. for 30 minutes. Cells were washed with HBSS/PBS three times, and secondary antibody horse radish peroxidase (HRP)-conjugated goat anti-mouse IgG purchased from Southern Biotechnology Associates (1:500 in HBSS/PBS+5% FBS) was added and incubated at 37° C. for 30 minutes. Cells were washed with HBSS/PBS four times and peroxidase substrate 3,3',5,5'-tetramethylbenzidine (TMB) was added and incubated in the dark at room temperature until there was adequate blue color development. The length of incubation time was typically 5–15 minutes. 2 N sulfuric acid was added to stop the color development and the data was collected by reading the absorbance at O.D. 450 nm. The result was expressed as the percentage of control sample (cells stimulated by TNF without any compound). IC50 is the concentration of compound required to inhibit 50% of the TNF stimulated signal.

The degree of inhibition of various compounds, including the compounds prepared in the foregoing examples, using the assays described in Examples 6–9, are provided in Table IX. Results are expressed in micromolar quantities. For example, a VCAM $IC_{50}$ of 3 for a particular compound means that such compound inhibits 50% of the maximum expression rate of VCAM-1 at a concentration of 3 micromolar.

TABLE IX

| Compound | VCAM-1 $IC_{50}$ or % inhibition at (uM) | $LD_{50}$ at (uM) | ApoB/Hep G2 $IC_{50}$ or % inhibition at [uM] |
|---|---|---|---|
|  | 12.5 | 25.0 | 6.0 |

TABLE IX-continued

| Compound | VCAM-1 IC$_{50}$ or % inhibition at (uM) | LD$_{50}$ at (uM) | ApoB/Hep G2 IC$_{50}$ or % inhibition at [uM] |
|---|---|---|---|
| (structure) | 8.0 | N/D | N/D |
| (structure) | 7.0 | 50.0 | 30.0 |
| (structure) | 10.0 | 50.0 | N/D |
| (structure) | 12.5 | 50.0 | 85.0 |
| (structure) | 12.5 | N/D | 40.0 |

*N/D—Not determined

Pharmaceutical Compositions and Modes of Administration

Animals, including mammals and specifically humans, suffering from any of the above-described conditions can be treated by the topical, systemic or transdermal administration of a composition comprising an effective amount of the compound of formula (I) or formula (II) or a pharmaceutically acceptable salt thereof, optionally in a pharmaceutically acceptable carrier or diluent.

The composition is administered subcutaneously, intravenously, intraperitoneally, intramuscularly, parenterally, orally, submucosally, by inhalation, transdermally via a slow release patch, or topically, in an effective dosage range to treat the target condition. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the herein described conditions are those ranging from 0.1 mg/kg to 500 mg/kg of body weight per day as a single daily dose or divided daily doses. Dosages for the described conditions range from 5–1500 mg per day. A more particular dosage for the desired conditions ranges from 25–750 mg per day. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A particular mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials which do not impair the desired action, or with materials that supplement the desired action. The active compounds can be administered in conjunction with other medications used in the treatment of cardiovascular disease, including lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol, N-ethyl-2-pyrrolidone or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

If administered intravenously, exemplary carriers include physiological saline, bacteriostatic water, Cremophor EL™ (BASF, Parsippany, N.J.) or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also exemplary as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Modifications and variations of the present invention relating to compounds that inhibit the suppression of VCAM-1 and methods of treating diseases and disorders mediated by the expression of VCAM-1 will be obvious to those skilled in the art from the foregoing detailed description of the invention. Such modifications and variations are intended to come with the scope of the appended claims.

What is claimed is:

1. A compound of formula (1), or a pharmaceutically acceptable salt thereof:
wherein
    a) Ra Rb Rc and Rd are independently any group that does not adversely affect the desired properties of the molecule, including hydrogen, alkyl, substituted alkyl, aryl, substituted aryl, heteroaryl, substituted heteroaryl, alkaryl, substituted alkaryl, arakyl, or substituted aralkyl; and
    b) Z is (i) a substituted or unsubstituted carbohydrate, (ii) a substituted or unsubstituted alditol, (iii) C1–10 alkyl or substituted C1–10 alkyl, terminated by sulfonic acid, or ii) C1 alkyl or substituted C1–10 alkyl, terminated by phosphonic acid, (v) substituted or unsubstituted C1–10 alkyl OC(O)C1–10 alkyl, (vi) straight chained polyhydroxylated C2–10 alkyl; (vii) (CR2)1–6COOH, wherein R is independently hydrogen, hale, amino, or hydroxy, and wherein at least one of the R substituents is not hydrogen; or (viii) (CR2)1–6X, wherein X is aryl, heteroaryl, or heterocycle, and R is independently hydrogen, hale, amine, or hydroxy.

2. The compound of claim 1 wherein Ra Rb Rc and Rd are t-butyl.

3. The compound of claim 1 wherein Z is —(CR2)1–6-sulfonic acid, and R is independently hydrogen, halo, amino, or hydroxy.

4. The compound of claim 1 wherein Z is —(CR$_2$)$_{1-6}$-phosphonic acid, and R is independently hydrogen, halo, amino, or hydroxy.

5. The compound of claim 1 wherein Z is —(CR$_2$)$_{1-4}$-phosphonic acid, and R is independently hydrogen, halo, or hydroxy.

6. The compound of claim 1 wherein $R_a$, $R_b$, $R_c$, and $R_d$ are t-butyl, and Z is 2-hydroxypropan-3-sulfonic acid.

7. A pharmaceutical composition comprising the compound of claim 1 and a pharmaceutically acceptable carrier.

8. The pharmaceutical composition of claim 7 wherein $R_a$, $R_b$, $R_c$, and $R_d$ are t-butyl, and Z is 2-hydroxypropan-3-sulfonic acid.

9. The pharmaceutical composition of claim 7 wherein $R_a$, $R_b$, $R_c$, and $R_d$ are t-butyl.

10. The compound of claim 1 wherein Z is:

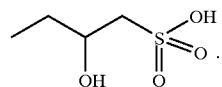

11. The compound of claim 1 wherein Z is —CH$_2$PO$_3$H$_2$.

12. The compound of claim 1 wherein Z is CH$_2$PO$_3$H$_2$.

13. The compound of the following structure:

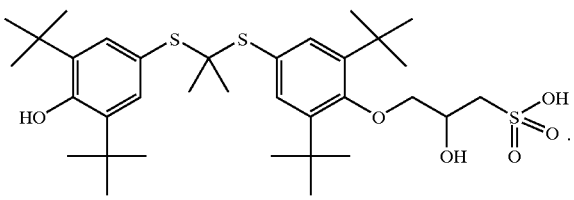

14. The composition of claim 7 wherein the composition is suitable for oral administration.

15. The composition of claim 7 wherein the composition is suitable for intravenous administration.

16. The composition of claim 7 wherein the compound is in a dosage unit.

17. The composition of claim 16 wherein the dosage form is a tablet or capsule.

18. The composition of claim 16 wherein the dosage unit contains 5–1500 mg of active ingredient.

19. The composition of claim 7 further comprising another medication use in the treatment of cardiovascular disease.

20. The composition of claim 19 wherein the other medication is a lipid lowering agent.

21. The composition of claim 19 wherein the other medication is a platelet aggregation inhibitor.

22. The composition of claim 19 wherein the other medication is a antithrombotic agent.

23. The composition of claim 19 wherein the other medication is a calcium channel blocker.

24. The composition of claim 19 wherein the other medication is a angiotensin converting enzyme inhibitor.

25. The composition of claim 19 wherein the other medication is a β-blocker.

26. The composition of claim 19 wherein the other medication is a non-steroidal anti-inflammatory.

27. The composition of claim 19 wherein the other medication is a selected from the group consisting of probucol, nicotinic acid, aspirin, coumadin, varapamil, diltiazam, nifedipine, captopril, enalopril, propanalol, tebutalol, labetalol, ibuprofen, indomethacin, fenoprofen, mefenamic acid, flufenamic acid, sulindac, corticosteroid.

* * * * *

UNITED STATES PATENT AND TRADEMARK OFFICE
CERTIFICATE OF CORRECTION

PATENT NO. : 6,852,878 B2  Page 1 of 1
APPLICATION NO. : 09/815262
DATED : February 8, 2005
INVENTOR(S) : Charles Q. Meng et al.

It is certified that error appears in the above-identified patent and that said Letters Patent is hereby corrected as shown below:

Title Page, Item (75)
In the list of inventors --James A. Sikorski, Alpharetta, GA-- should be inserted Column 43, line 22, insert the following formula:

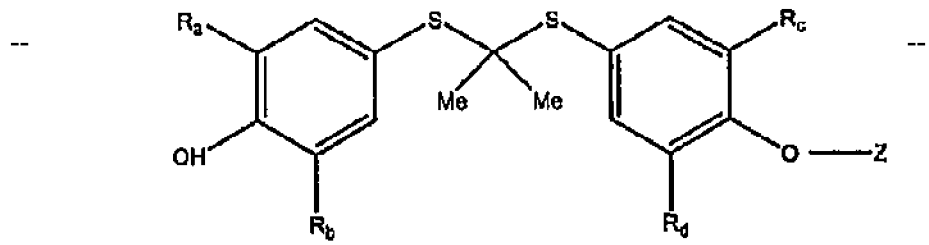

Column 43, line 30, cancel the text beginning with "a substituted or unsubstituted carbohydrate" to and ending with "or hydroxy", in column 43, line 42, insert the following text: --C1-10 alkyl or substituted C1-10 alkyl, terminated by sulfonic acid, or (ii) C1-10 alkyl or substituted C1-10 alkyl, terminated by phosphonic acid.--

Signed and Sealed this

Twelfth Day of June, 2007

JON W. DUDAS
*Director of the United States Patent and Trademark Office*